United States Patent
Koch et al.

(10) Patent No.: US 6,436,908 B1
(45) Date of Patent: Aug. 20, 2002

(54) USE OF EXOGENOUS β-ADRENERGIC RECEPTOR AND β-ADRENERGIC RECEPTOR KINASE GENE CONSTRUCTS TO ENHANCE MYOCARDIAL FUNCTION

(75) Inventors: Walter J. Koch; Robert J. Lefkowitz; Carmelo A. Milano, all of Durham; Howard A. Rockman, Chapel Hill, all of NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/285,677

(22) Filed: Apr. 5, 1999

Related U.S. Application Data

(63) Continuation of application No. 08/453,202, filed on May 30, 1995, now abandoned.

(51) Int. Cl.$^7$ ................................................ A61K 31/70

(52) U.S. Cl. ...................... 514/44; 424/93.2; 435/320.1; 435/455; 435/458

(58) Field of Search ........................... 514/44; 424/93.2; 435/320.1, 455, 458; 536/23.1, 23.4

(56) References Cited

FOREIGN PATENT DOCUMENTS

| EP | 0351921 | 1/1990 |
|---|---|---|
| EP | 0453119 | 10/1991 |

OTHER PUBLICATIONS

Crystal, "Transfer of Genes to Humans: Early Lessons and Obstacles to Success", Science 270:404–410 (1995).

Marshall, "Less Hype, More Biology Needed for Gene Therapy", Science 270:1751 (1995).

Coghlan, "Gene dream fades away", New Scientist 148:14–15 (1995).

Güsburg et al, "Virus vector design in gene therapy", Molecular Medicine Today pp. 410–417 (1995).

Froecking et al, "Powerful and versatile enhancer–promoter unit for mammalian expression vectors", Gene 45:101–105 (1986).

Koch et al, "Cellular Expression of the Carboxyl Terminus of a G Protein–coupled Receptor Kinase Attenuates Gβγ–mediated Signaling", J. Biological Chem. 269:6193–6197 (1994).

Lee et al, "Cardiac and Pulmonary Replacement", J. Thoracic Cardiovascular Surgery 111(1):246–252 (1996).

Fuller et al, "Genetic Engineering of Cardiac Muscle Cells: In Vitro and In Vivo", Genetic Engineering 16:17–27(1994).

Luckow et al, "CAT constructions with multiple unique restriction sites for the functional analysis of eukaryotic promoters and regulatory elements", Nucleic Acids Research 15(13):5490 (1987).

Ngo et al, "Computational Complexity, Protein Structure Prediction, and the Levinthal Paradox", The Protein Folding Problem and Tertiary Structure Prediction, K. Merz, Jr. and S. Le Grand, Editors, Birkhauser Bost Inc., pp. 491–495 (1994).

Dillon, "Regulating gene expression in gene therapy", TIBTECH 11:167–173 (1993).

Rigby, "Gene therapy: a long and winding road", Current Opinion in Genetics and Development 5:397–398 (1995).

Orkin et al, "Report and Recommendations of the Panel to Assess the NIH Investment in Research on Gene Therapy", pp. 1–50, Dec. 7, 1995.

Kobilka et al., "cDNA for the human $β_2$–adrenergic receptor: A protein with multiple . . . ," Proc. Natl. Acad. Sci. USA, vol. 84, Jan. 1987, pp. 46–50.

Kass–Eisler et al., "Quantitative determination of adenovirus–mediated gene delivery . . . ," Proc. Natl. Acad. Sci. USA, vol. 90, Dec. 1993, pp. 11498–11502.

Stratford–Perricaudet et al., "Widespread Long–term Gene Transfer to Mouse Skeletal . . . ," J. Clin. Invest., vol. 90, Aug. 1992, pp. 626–630.

Guzman et al., "Efficient Gene Transfer into Myocardium by Direct Injection of Adenovirus Vectors," Circulation Research, vol. 73, 1993, pp. 1202–1207.

Bertin et al., "Specific atrial overexpression of G protein coupled human $β_1$ adrenoceptors . . . ," Cardiovascular Research, vol. 27, 1993, pp. 1606–1612.

Metzger et al, "Skeletal troponin C reduces contractile sensitivity to acidosis in cardiac . . . ," Proc. Natl. Acad. Sci. USA, vol. 90, Oct. 1993, pp. 9036–9040.

Ren et al., "Constitutively Active Mutants of the $α_2$–Adrenergic Receptor," The Journal of Biological Chemistry, vol. 268, No. 22, Aug. 5, 1993, pp. 16483–16487.

Pauletto et. al., "Propranolol–induced changes in ventricular isomyosin composition in the rat," American Heart Journal, vol. 109, Jun. 1985, pp. 1269–1273.

Bristow et al., "Decreased Catecholamine Sensitivity and β–Adrenergic–Receptor . . . ," The New England Journal of Medicine, vol. 307, No. 4, Jul. 22, 1982, pp. 205–211.

(List continued on next page.)

*Primary Examiner*—Dave T. Nguyen
(74) *Attorney, Agent, or Firm*—Nixon & Vanderhye P.C.

(57) ABSTRACT

The present invention deals with gene therapy for treating chronic heart failure and other cardiac disease states which are accompanied by a reduced number or functioning of myocardial beta-adrenergic receptors (β-AR). β-AR receptor function is augmented in transgenic animals by delivery and expression of a beta-2-adrenergic receptor gene or a gene encoding a beta adrenergic receptor kinase inhibitor, resulting in increased in vivo left ventricular function. The present invention includes recombinant plasmid vectors, alternative beta-adrenergic receptor gene delivery strategies, and transgenic mice carrying a β-AR transgene, a β-ARK transgene, or a β-ARK inhibitor transgene.

15 Claims, 13 Drawing Sheets

OTHER PUBLICATIONS

Bristow et al., β–Adrenergic Function in Heart Muscle Disease and Heart Failure, J. Mol. Cell. Cardiol. 17 (Supp. 2), 1985, pp. 41–52.

Bristow et al., "β–Adrenergic Pathways in Nonfailing and Failing Human Ventricular Myocardium," Circulation, vol. 82 (Suppl. I), 1990, pp. I–12–I–25.

Fowler et. al., "Assessment of the β–adrenergic receptor pathway in the intact failing human heart:...," Circulation, vol. 74, No. 6, Dec. 1986, pp. 1290–1302.

Ungerer et al., "Altered Expression of $\beta_1$ –Adrenergic Receptor Kinase and β–Adrenergic ..." Circulation, vol. 87, 1993, pp. 454–463.

Koch et al., "The Binding Site for the βT Subunits of Heterotrimeric G Proteins ...," The Journal of Biological Chemistry, vol. 268, No. 11, Apr. 15, 1993, pp. 8256–8260.

Benovic et al., "β–Adrenergic Receptor Kinase: Primary Structure Delineates a Multigene Family,"Science, vol. 246, Oct. 13, 1989, pp. 235–240.

Hausdorff et al., "Turning off the signal: desensitization of β–adrenergic receptor function," The FASEB Journal, vol. 4, Aug. 1990, pp. 2881–2889.

Lohse et al., "Multiple Pathways of Rapid $\beta_2$–Adrenergic Receptor Desensitization," The Journal of Biological Chemistry, vol. 265, No. 6, Feb. 25, 1990, pp. 3202–3209.

Inglese et al., "Structure and Mechanism of the G Protein–coupled Receptor Kinases," The Journal of Biological Chemistry, vol. 268, No. 32, Nov. 15, 1993, pp. 23735–23738.

Ng et al., "Cardiac Myosin Heavy Chain mRNA Expression and Myocardial Function in the Mouse Heart," Circulation Research, vol. 68, No. 6, Jun. 1991, pp. 1742–1750.

Medford et al., "Molecular Mechanisms Regulating VCAM–1, ICAM–1 and E–Selectin Gene Expression in Human Aortic Smooth Muscle Cells", Clinical Research, vol. 41, No. 2, 1993, p. 145A.

Pitcher et al., "Role of βT Subunits of G Proteins in Targeting the β–Adrenergic...,"Science, vol. 257, Aug. 28, 1992, pp. 1264–1267.

Yatani et al., "A G Protein Directly Regulates Mammalian Cardiac Calcium Channels," Science, vol. 238, Nov. 1987, pp. 1288–1292.

USE OF EXOGENOUS β-ADRENERGIC RECEPTOR AND β-ADRENERGIC RECEPTOR KINASE GENE CONSTRUCTS TO ENHANCE MYOCARDIAL FUNCTION

This application is a continuation of application Ser. No. 08/453,202, filed May 30, 1995; now abandoned.

The work described in this patent application was supported in part by NIH grants HL-16037, HL 5F32-CA09350 and by the American Heart Association, California affiliate grant 94-286. The government has certain rights in the invention.

FIELD OF THE INVENTION

The present invention relates generally to gene therapy for treating chronic heart failure or other cardiac diseases associated with decreased myocardial β-adrenergic receptors and reduced myocardial function. More particularly, this invention relates to manipulation of genes and gene products that affect β-adrenergic receptors in myocardium in order to enhance myocardial function. The invention also relates to receptors, methods or systems for drug screening, and transgenic animals suitable for investigation of therapies for treatment of heart failure and other cardiac conditions.

BACKGROUND INFORMATION

G-protein-coupled receptors, such as the adrenergic receptors, elevate cellular levels of second messengers like cyclic-adenosine monophosphate (cAMP) and diacylglycerol thereby regulating and coordinating cellular metabolism and function. In the heart, β-adrenergic receptors (β-ARs), responsive to the sympathetic neurotransmitter norepinephrine and the adrenal medullary hormone epinephrine, stimulate adenylyl cyclase, raising myocardial cAMP and increasing cardiac contractility. Elevated circulating catecholamines and myocardial β-AR stimulation represent critical mechanisms for augmenting cardiac function during stress.

As is true for most G protein-coupled receptors, prolonged agonist exposure of β-ARs leads to a rapid decrease in responsiveness. Agonist-dependent desensitization can be initiated by phosphorylation of activated receptors by members of the G protein-coupled receptor kinase (GRK) family (W. P. Hausdorff et al., *FASEB J.* 4, 2881 (1990); J. Inglese et al., *J. Biol. Chem.* 268, 23735 (1993)). Phosphorylated receptors then interact with arresting proteins like β-arrestin to which they bind thereby sterically interdicting further coupling to G proteins (W. P. Hausdorff et al., 1990; J. Inglese et al., 1993). The β-adrenergic receptor kinase-1 (βARK1) is a GRK which has been shown to specifically phosphorylate activated β2-ARs in vitro and which is hypothesized to phosphorylate $β_2$-ARs in vivo leading to uncoupling and desensitization (W. P. Hausdorff et al., 1990; J. Inglese et al., 1993; M. J. Lohse et al., *Proc. Natl. Acad. Sci. U.S.A.* 86, 3011 (1989); M. J. Lohse et al., *J. Biol. Chem.* 265, 3202 (1990); S. Pippig et al., *J. Biol. Chem.* 268, 3201 (1993)).

The action of βARK1 on the $β_1$-AR has not yet been documented. βARK1 is specifically targeted to activated receptors in the plasma membrane by a translocation event mediated via a specific protein-protein interaction between the carboxyl terminus of the kinase and the βγ subunits of activated and dissociated G proteins (J. Pitcher et al., *Science* 257, 1264 (1992); W. J. Koch et al., *J. Biol. Chem.* 268, 8256 (1993)).

In chronic congestive heart failure, an illness affecting more than four million Americans, there is dramatic impairment of the myocardial β-AR system. Failing human ventricular myocardium contains 50% fewer β-ARs and shows parallel decreases in agonist-stimulated adenylyl cyclase activity and even greater decreases in agonist-mediated inotropy (M. R. Bristow et al., *N. Engl. J. Med.* 307, 205 (1982), M. R. Bristow et al., *J. Mol. Cell. Cardiol.* 17 (Suppl. 2), I12 (1990)). In addition, increases in inhibitory G-protein and G-protein receptor kinases (e.g. β-adrenergic receptor kinase) in heart failure may further impair receptor-mediated inotropy (T. Eschenhagen et al., *Circulation Research* 70, 688 (1992) and M. Ungerer et al., *Circulation* v7, 454 (1993)). Therapeutic interventions, involving the administration of agonists to stimulate the β-AR/adenylyl cyclase systems have an inherently limited efficacy given the reduction in receptor targets in the diseased myocardium.

An additional possible contributor to the decreased myocardial β-AR responsiveness seen in chronic failing human hearts is that levels of βARK1 are elevated (M. Ungerer et al., *Circulation* 87, 454 (1993); M. Ungerer et al., *Circ. Res.* 74, 206 (1994)). Thus, β-AR impairment in heart failure may have several underlying causes.

The field of transgenic technology has achieved significant advances in techniques for in vivo gene transfer in recent years (T. Ragot et al., *Nature* 361, 647 (1993); M. A. Rosenfeld et al., *Cell* 68, 143 (1992); R. J. Guzman, et al., *Circulation Research* 73, 1202 (1993)).

While several transgenic mice have been reported which express, for example, the c-myc proto-oncogene or SV-40 T-antigen affecting cardiac growth (J. L. Swain et al., *Cell* 50, 719 (1987); L. J. Field, *Science* 239, 1029 (1988); E. B. Katz et al., *Am. J. Physiol.* 262, H1867 (1992)), to date there have been no reports concerning the ability of a transgene to affect myocardial contractility.

SUMMARY OF THE INVENTION

The present invention provides novel strategies for improving cardiac function, for example by overexpressing the β-AR in the myocardium, or by inhibiting the activity of βARK. It utilizes molecular, in vitro and in vivo methodologies to assess the biochemical and physiological consequences of transgenic overexpression of the human $β_2$-AR in the heart. In addition, the invention utilizes in vitro and in vivo methodologies to assess the consequences of overexpression or suppression of βARK in the heart.

In general, the invention features gene therapy for disease states where specific receptor-mediated functions are lost or altered. In particular, defects in the β-adrenergic receptors (B-AR) and in inotropic responsiveness in heart failure are a therapeutic target.

The invention provides a method for the delivery of a gene for β-AR, e.g., $β_2$-AR, and a "minigene" encoding a βARK inhibitor for delivery to diseased heart tissue. The invention also provides transgenic mice with cardiac specific overexpression of β-AR or βARK, and mice with cardiac specific expression of a βARK inhibitor. In addition, the invention provides a means for screening drugs that may be useful in the treatment of heart disease.

According to the invention, gene transfer to heart tissue may be accomplished by in vivo methods of gene transfer such as those involving the use of recombinant replication deficient adenovirus. Procedures include gene transfer into cardiac muscle are described in the literature, for example in Kass-Eisler, A. et al., *Proc. Natl. Acad. Sci. U.S.A.,* 90: 11498–11502 (1993); Stratford-Perricaudet, L. D. et al., *J. Clin. Invest.* 90: 626–630 (1992); and Guzman, R. J. et al., *Circ. Res.* 73: 1201–1207 (1993).

The gene for the human $\beta_2$-AR has been cloned (Kobilka, B. K. et al., *Proc. Natl. Acad. Sci. U.S.A.* 84:46–50) and in the present invention, the $\beta$-AR gene, e.g., $\beta_2$-AR or other subtypes, is simply any nucleic acid sequence which codes for a $\beta$-AR, said receptor having the ability to couple to adenylyl cyclase. Thus variations in the actual sequence of the gene can be tolerated provided that the $\beta$-AR can be expressed and is able to couple to adenylyl cyclase.

A $\beta$-AR gene construct can be obtained through conventional recombinant DNA techniques.

It is an object of the present invention to provide transgenic mice whose germ cells and somatic cells contain overexpressed human $\beta$-AR in the heart, transgenic mice whose germ cells and somatic cells contain genes for cardiac overexpression of $\beta$ARK, and transgenic mice whose germ cells and somatic cells contain a gene for cardiac expression of a $\beta$ARK inhibitor. The transgenic mice of the invention will usually have expressed levels of the gene products in myocardial tissue that are at least 50% greater, and preferably at least 100% greater, than levels than would normally occur in mice. In addition, the transgenic mice's myocardial function (e.g. heart rate or contractility) can be increased or decreased by about 10% and preferably by about 20% as desired.

Transgenic mice in the present invention were created by microinjection of the desired gene construct into the pronuclei of one cell embryos, which were then surgically re-implanted into pseudo-pregnant female animals. There are several means by which transgenic animals can be made. One method employs the embryonic stem cell methodology known to workers in this field.

Preferably, transcription of the $\beta$-AR gene is controlled by a promoter which generates intense cardiac expression. Example of such promoter sequences include, in mice, the $\alpha$-myosin heavy chain promoter and in larger mammals the CMV (cytomegalo virus) promoter or the $\beta$-myosin heavy chain promoter. These examples are not meant to be limiting but rather represent currently available promoters which are felt to be capable of expressing the $\beta$-AR at levels above the endogenous, background myocardial $\beta$-AR levels.

According to the present invention transgenic mice were created in which the $\alpha$-myosin heavy chain promoter was utilized to direct intense cardiac specific expression of the human $\beta_2$-adrenergic receptor (ranging from 50 to 200 fold above control levels in three separate transgenic mouse lines). This resulted in dramatic elevation of myocardial adenylyl cyclase activity, enhanced atrial myocardial contractility and increased in vivo left ventricular function; these three parameters at baseline in the transgenic animals, were equal to those observed in control animals maximally stimulated with the $\beta$-agonist, isoproterenol.

Accordingly, it is an object of the present invention to provide a recombinant vector for myocardial tissue expression of the $\beta$-AR gene.

Preferably, transcription of the $\beta$-AR gene coding sequence is controlled by a promoter sequence which generates selective cardiac expression. Examples of such promoter sequences include, in mice, the $\alpha$-myosin heavy chain promoter and, in humans, the CMV (cytomegalo virus) promoter, or the $\beta$-myosin heavy chain promoter. For general use, any promoter which gives large expression or promoter which is only operational in the heart such as those from the genes for $\alpha$ and $\beta$ myosin heavy chain and myosin light chain is suitable. These can be obtained by gene cloning techniques and promoter:fusion gene assays known to those skilled in the art. Typical of these include studies done to characterize promoter regions for the $\alpha$-myosin heavy chain (Subramian et al., *J. Biol. Chem.* 266, 24613 (1991) and myosin light chain (Lee et al. *J. Biol. Chem.*, 267, 15875 (1992)).

It is another object of the present invention to provide host cells stably transformed or transfected with the above-described recombinant constructs. The host cell can be prokaryotic (for example, bacterial), lower eukaryotic (for example, yeast or insect), or higher eukaryotic (for example, all mammals, including but not limited to mouse and human). For instance, transient or stable transfections can be accomplished into mammalian myocardial myocytes. Transformation or transfection can be accomplished using protocols and materials known in the art. The transformed or transfected host cells can be used as a source of the recombinant construct.

Transfected cells as described above, such as mammalian myocardial myocytes transformed with a recombinant construct can also be used to treat heart disease by transplanting the transformed myocardial myocytes which express $\beta$-AR into a diseased heart tissue. The objective of such. therapy is to increase the heart function of a patient (e.g. strength of contraction) by at least 10%, and preferably by 20% or more.

Thus, it is another object of the invention to provide treatment for heart disease using a myocardial myocyte transformed as described above for transplanting into a diseased heart. Myocytes in culture can be transformed by standard techniques to contain the gene products of the invention. These cells can be delivered to intact myocardium by techniques similar to other muscle grafts and when accepted by the host organ would improve cardiac function by replacing damaged cells with "supercharged" cells.

It is yet another object of the present invention to provide transgenic animals with myocardial overexpression of the human beta-adrenergic receptor. Such transgenic animals can be used as models to study myocardial function and to determine whether increased myocardial $\beta$-AR provides resistance to the development of heart failure or ventricular overload. Further, a transgenic mouse according to the present invention can be used to test for agents which decrease heart rate, or block $\beta$-AR.

It is yet another object of the invention to provide gene therapy for the treatment of chronic heart failure which is associated with decreased $\beta$-ARs.

It is still another object of the invention to provide resistance to heart failure in mammals (experimental animals) by administering the exogenous genes which will increase myocardial $\beta$-AR.

It is yet another object of the present invention to provide improved heart function in mammals which exhibit weakened heart function associated with a low number of $\beta$-AR receptors, diminished functional activity of the mammals own $\beta$-ARs, or decreased contractile function of the left ventricle.

It is a further object of the present invention to provide transgenic animals with myocardial overexpression of $\beta$ARK. According to the present invention, transgenic mice were created in which the $\alpha$-myosin heavy chain promoter was utilized to direct cardiac specific expression of a coding sequence for the entire coding region for bovine $\beta$ARK. These mice display marked attenuation of isoproterenol stimulated left ventricular contractility in vivo, and other signs of reduced functioning of the myocardial $\beta$-AR system. Such animals have utility for screening potential drugs and therapies to be used for the treatment of heart disease.

Thus, it is a further object of the invention to provide a recombinant vector for myocardial expression of a $\beta$ARK inhibitor.

It is yet a further object of the invention to provide a transgenic animal with myocardial expression of a βARK inhibitor. According to the present invention, transgenic mice were created in which the α-myosin heavy chain promoter was utilized to direct cardiac specific expression of a coding sequence for the carboxyl terminal portion of bovine βARK which inhibits the activity of the endogenous βARK. These mice display markedly enhanced cardiac contractility in vivo, even in the absence of a β-agonist.

Therefore, it is yet another object of the invention to provide a recombinant vector for myocardial expression of a βARK inhibitor. Such vectors can be used therapeutically for conditions where enhancement of functioning in the cardiac β-AR system is desired.

In the present invention, the βARK gene is any nucleic acid sequence which encodes βARK, an enzyme that desensitizes β-ARs through a process that involves phosphorylation. A βARK inhibitor, according to the invention, is any substance that can be delivered to tissue through genetic means that will inhibit the production or functioning of βARK. A gene for βARK has been cloned (J. L. Benovic et al., Science 246, 235 (1989)), and βARK gene construct and βARK minigene construct can be obtained through conventional recombinant DNA techniques.

The present invention utilizes βARK1, which is the primary βARK in the heart. Bovine, mouse, and human βARK1 have identical functional properties (J. Inglese et al., J. Biol. Chem., 268, 23735 (1993)). The open reading frame of the human βARK cDNA encodes a protein of 689 amino acids which has 98% amino acid and 92.5% nucleotide identity to bovine βARK (J. L. Benovic et al., FEBS Lett. 283, 122–126 (1991)). Thus, although bovine βARK has been used in the examples, the invention includes the claimed vectors, constructs, methods and transgenic animals as made with other βARK sequences, and in particular with the human sequence.

Preferably, transcription of the ARK gene and the βARK inhibitor "minigene" is controlled by a promoter which generates intense cardiac expression. Examples of such promoter sequences include, in mice, the α-myosin heavy chain promoter and in larger mammals the CMV promoter or the β-myosin heavy chain promoter. Other promoters which result in cardiac-specific expression will also be suitable.

Other features and advantages of the invention will be apparent from the detailed description of the invention, and from the claims. The complete contents of references cited herein are hereby incorporated by reference.

BRIEF DESCRIPTION OF THE DRAWINGS

FIG. 6B: heart rate (HR); FIG. 6C: mean aortic pressure); data are reported as mean±S.D. Data were analyzed with a two-way repeated measures ANOVA with post hoc tests based on t-test with Bonferroni correction for 5 comparisons (p<0.05 was considered significant). At baseline TG4 LV $dP/dt_{max}$ was markedly increased compared to controls (p<0.005), and did not change with isoproterenol (panel A). In contrast, the control animals demonstrated the expected, progressive increase in LV $dP/dt_{max}$ with isoproterenol, and control $dP/dt_{max}$ did not differ from TG4 $dP/dt_{max}$ at the highest isoproterenol dose. Under baseline conditions, TG4 HR was markedly increased relative to controls (p<0.005) and remained significantly greater throughout the isoproterenol administration (panel B). With the highest dose of isoproterenol, there was significant decline in mean aortic pressure in the TG4 animals relative to controls.

The sequence of Trip$^{643}$ to Ser$^{670}$ (WKKELRDAYREAQQLVQRVPKMKNKPRS) is given in SEQ ID NO:1. The sequence of βARK1 residues 495 to 689 is given in SEQ ID NO:2.

FIG. 11. Effect of βARK1 transgene expression on β$_1$-AR receptor-effector coupling. (A) Isoproterenol competition binding isotherms with sarcolemmal membranes prepared from the hearts of TGβK12 and non-transgenic littermate controls. Isotherms were carried out with 75 nM ICI 118,551 to inhibit the β$_2$-AR component of binding and in the absence or presence of GTP (100 μM). Data shown is the mean±SEM of duplicate determinations from 3–9 hearts. (B) Adenylyl cyclase activity in sarcolemmal membranes of TGβK12 and control hearts was determined under basal conditions and in the presence of progressive doses of isoproterenol or 10 mM NaF (C. A. Milano et al., Science 264, 582 (1994)). Membranes (5–20 μg protein) were incubated for 10 min at 37° C. and [α-$^{32}$P]ATP was isolated and quantitated (Y. Salomon et al., Anal. Biochem. 58, 541 (1974). All assays contained 50 nM ICI 118,551 previously shown to selectively inhibit the β$_2$ component of cyclase activation (H. Lemoine et al., Nauy-Schmeideberg's Arch. Pharmacol. 331, 40 (1985). Basal and isoproterenol-stimulated cyclase values were normalized to the percentage of activation achieved with NaF which was not significantly different between transgenic and control membranes. Data shown is the mean±SEM of duplicate determinations of 3 hearts. * denotes statistical significance (P<0.05) analyzed via a students t-test.

FIG. 12. In vivo assessment of left ventricular function of TGβK12 (n=10) and nontransgenic control mice (n=10). Animals were anesthetized and aortic and left ventricular catheters placed (28). Four measured parameters are shown at baseline and after progressive doses of isoproterenol: (A) LV dP/dt$_{max}$; (B) LV dP/dt$_{min}$; (C) heart rate (HR); and (D) LV systolic pressure. Data are reported as means±SEM and were analyzed with a two way analysis of variance (ANOVA) with post hoc testing performed using Scheffe's F test (*, P<0.05). When the entirety of the control and TGβK12 isoproterenol dose response curves were compared by ANOVA they were found to differ significantly for (A) dP/dt$_{max}$, P<0.001; (B) dP/dt$_{min}$, P<0.05; (C) HR, P<0.01 but not (D) LV systolic pressure, P=ns.

FIG. 13. In vivo assessment of left ventricular function of TGMini27 (n=7) and nontransgenic control mice (n=7). Mice were treated as in FIG. 4 (28) and four parameters are shown; (A) LV dP/dt$_{max}$; (B) LV dP/dt$_{min}$; (C) HR; and (D) LV systolic pressure. Data are reported as mean±SEM and were analyzed as in FIG. 4 (*, P<0.05). The entirety of control and TGMini27 isoproterenol dose response curves were found by ANOVA to differ significantly for (A) dP/dt$_{max}$, P<0.005; (B) dP/dt$_{min}$, P<0.005; and (D) LV systolic pressure, P<0.005.

DETAILED DESCRIPTION OF THE INVENTION

Transgene Construct for β-AR

Figure 1A:
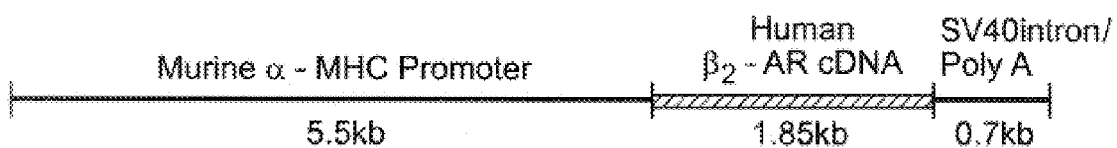
FIG. 1A: Transgenic construct containing human $β_2$-AR. A 5.5 kb Sacl-SalI fragment (consisting of the entire inter genic region between the murine β-MHC gene (upstream) and the α-MHC gene), was isolated from clone 20 (A. Subramanian et al., J. Biol. Chem. 266, 24613 (1991)) and ligated into a pGEM9Zf(−) vector, previously modified to contain the SV-40 intron/poly A signal, to generate pGEM-αMHC-SV40. A 1.85 kb SalI-SalI fragment consisting of the human $β_2$-AR cDNA was then isolated from pGEMβ2AR and ligated into the SalI site of pGEM αMHC-SV40 to generate pGEM-αMHC-$β_2$-SV40. This vector was then digested with SfiI and NotI to generate the linear 8.5 kb fragment used for microinjection.

The transgene construct (FIG. 1) for these experiments employed the murine alpha myosin heavy chain (α-MHC) promoter. This promoter has been shown to effect a pattern of transgene expression similar to the expression of the endogenous α-MHC, which is the predominant heavy chain isoform in adult murine atria and ventricles (A. Subramanian et al., J. Biol. Chem. 266, 24613 (1991)). This isoform is normally not expressed in smooth or skeletal muscle. In addition, it is not expressed in the ventricular chamber during development, and therefore potentially lethal developmental effects of β-AR activation could be avoided. Ligated to this promoter sequence was the cDNA for the human β$_2$-AR (FIG. 1A). Under normal conditions, β$_2$-ARs compose a small fraction of total myocardial β-ARs, which are predominantly of the β$_1$-AR subtype. However unlike β$_1$-ARs, β$_2$-ARs do not appear to undergo down regulation in clinical heart failure (a state of increased agonist stimulation); this has been shown both at the mRNA and the receptor protein level (M. Ungerer et al., Circulation 87, 454 (1993); M. R. Bristow et al., Circulation 82 (suppl I), 112 (1990)). Furthermore, the β$_2$-AR recently has been shown to couple to adenylyl cyclase with greater efficacy relative to the β$_1$-AR (F. O. Levy, et al. Proc. Natl. Acad. Sci. U.S.A. 90, 10798 (1993)). Finally, a previous attempt to overexpress myocardial β$_1$-ARs in transgenic mice resulted in only modest levels of expression without changes in contractility (B. Bertin et al., Cardiovascular Research 27, 1606 (1993)). Therefore, it appeared that overexpression (evidenced by increased levels of receptor) and phenotypic changes (including, but not necessarily limited to increased inotropy and chronotropy) were more likely to be achieved with the $\beta_2$-AR. The transgene construct was terminated with a portion of the SV-40 intron, which was included as 3' untranslated sequence to improve transcription and increase stability of the mRNA transcript. Very satisfactory results can be achieved without the latter step, which should be considered optional. In addition, globin introns, untranslated gene sequences and other methods known to those skilled in the art can also be used to achieve similar results.

This transgene construct was microinjected into the pronuclei of one cell mouse embryos, which were then surgically re-implanted into pseudo-pregnant female animals. Experiments with mice described in this report were conducted at three institutions (Duke University, University of Houston and the University of California at San Diego); in all cases institutional review board approval was obtained. Unless otherwise described Avertin (2.5% glen.) 0.015–0.017 ml/gm body weight i.p. was used for anesthesia, and 0.03 ml/gm used for sacrifice. Offspring were screened by Southern analysis using a probe to the SV-40 sequences, and three founders were identified containing the transgene. These founders demonstrated no gross phenotypic changes, and three lines with demonstrated transmission of the transgene were established (TG4, TG33 and TG35). Neonatal mortality in the transgenics did not differ from nontransgenic animals, and there were no adult deaths. Second generation adult animals, approximately 2–4 months of age, were used for the biochemical and physiologic studies. These animals had similar heart:body weight ratios relative to their litter mate controls and there was no evidence for developmental defects, myocyte necrosis or fibrosis.

Using these techniques or variations that are known to the skilled practitioner it is possible to routinely obtain several lines of transgenic mice.

Preparation of Myocardial Sarcolemmal Membranes

Myocardial sarcolemmal membranes were prepared by homogenizing whole hearts in ice-cold buffer A [50 mM HEPES (pH 7.3), 150 mM KCl, 5 mM EDTA]. Nuclei and tissue were separated by centrifugation at 800×g for 10 min and the crude supernatant was then centrifuged at 20,000×g for 10 min. The subsequent pellet was resuspended in buffer A and centrifuged at 20,000×g for 10 min. The final pellet was resuspended at a concentration of 2–3 mg protein per ml in buffer B [50 mM HEPES (pH7.3), 5 mM $MgCl_2$].

β-AR Transgene Expression

Figure 1B:
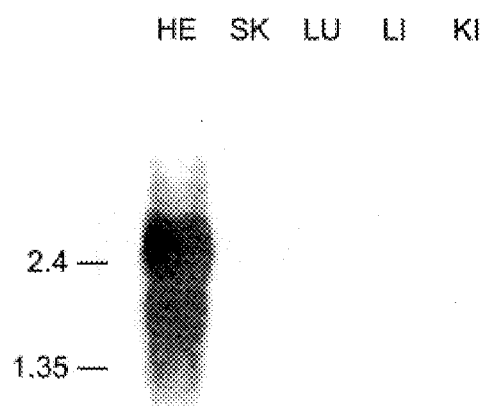
FIG. 1B: Total RNA was extracted from five tissues of second generation transgenic mice using the "RNAzol" method ("RNAzol" is a Tel-Test, Inc. trademark for a single-step method of RNA isolation first described by P. Chomcynski et al., Anal. Biochem. 162, 156 (1987)). Thirty micrograms of total RNA were loaded in each lane HE (heart), SK (quadriceps skeletal muscle), LU (lung), LI (liver) and KI (kidney), and fractionated on a 1.2% agarose/formaldehyde gel, then transferred to a nitrocellulose membrane, and prehybridized in a 50% formamide solution. Hybridization was conducted overnight with a random primer, [$α$-$^{32}$P] dCTP radio labeled, SV-40 intron DNA probe (1–2×10$^6$ cpm/ml). Following hybridization, the membrane was washed twice in 0.1×SSC at 65° C. for 30 minutes and exposed to film at −70° C. for 36 hrs. Autoradiography revealed a predominant band in the heart lane just above a 2.4 kb RNA marker, indicating the transgene mRNA of expected length. There is no evidence of transgene expression in the other tissues.
Figure 2A:
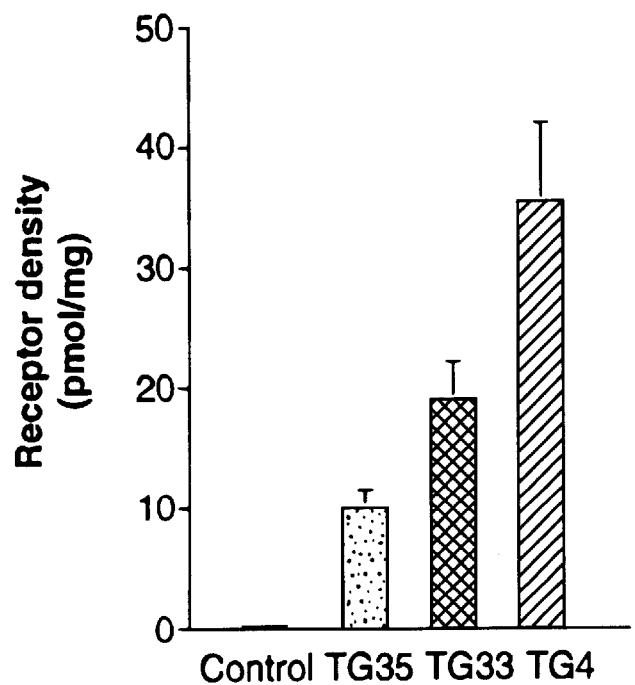
FIG. 2A. Transgene Expression Measured by Radioligand Binding. Crude myocardial membranes (Crude myocardial membranes were prepared in the following manner: whole hearts were homogenized in 5 ml of ice-cold lysis buffer(5 mM Tris Cl, pH7.4/5 mM EDTA/leupeptin 10 μg/ml/aprotinin 20 μg/ml). Nuclei and cellular debris were spun down at 500×g for 15 minutes, the supernatant was then passed through a double layer of cheese cloth and membranes were then pelleted by centrifugation at 40,000×g for 15 minutes. Membranes were washed with 5 mls of binding buffer (75 mM Tris Cl pH7.4, 12.5 mM MgCl$_2$, and 2 mM EDTA) and then resuspended in fresh binding buffer at approximately 1 mg membrane protein/ml). Membrane fractions were generated from 18 hearts from animals approximately 2 months of age (nontransgenic wild-type controls n=5, TG35 n=3, TG33 n=6, and TG4 n=4). Saturation ligand binding assays were performed in duplicate on crude membranes in 500 μl of binding buffer; each reaction contained saturating quantities of the β-AR radioligand, [$^{125}$I] CYP (approximately 500 pM, specific activity 2200 Ci/mmol), and nonspecific binding was determined in the presence of 20 μM alprenolol. Binding assays were conducted at 37° C. for 60 min. and terminated by rapid vacuum filtration over glass fiber filters, which were subsequently washed and counted in a gamma counter. Specific binding (estimated $B_{max}$) was normalized to membrane protein which was determined by the method of Bradford (M. M. Bradford, Anal. Biochem. 72, 248 (1976)) and reported as the mean picomoles of receptor/mg membrane protein±SEM. The nontransgenic control value which is poorly shown on the graph, was 0.18±0.04 pmol/mg.

Transgene expression assessed by Northern analysis on total RNA from whole heart, skeletal muscle, lung, liver and kidney, demonstrated intense cardiac transgene expression with no detectable expression in the other tissues (FIG. 1B). Transgene expression was quantitated by ligand binding assays (FIG. 2A), which demonstrated dramatic overexpression in all three lines; total β-AR levels ranged from approximately 55 times (TG35) to 195 times (TG4) control levels. The extraordinarily high expression was present in all three lines and therefore cannot be attributed to the site of genomic insertion (i.e. adjacent positive regulatory elements). These high receptor levels are due to the promoter or to properties of the mRNA transcript or receptor protein.

Figure 2B:
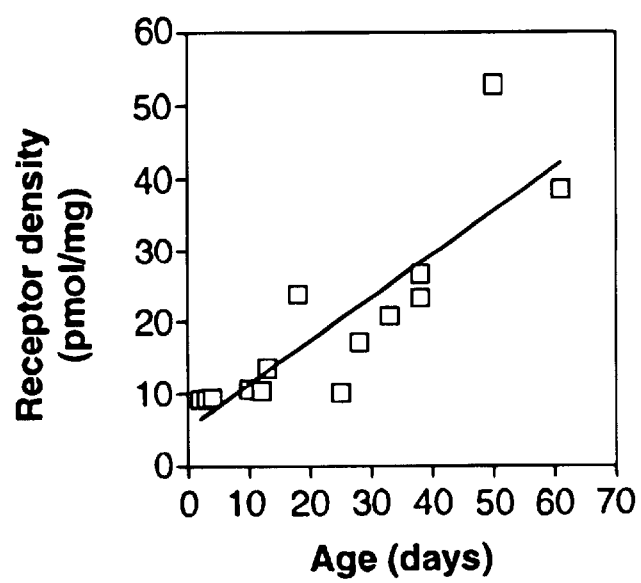
FIG. 2B. Estimated $B_{max}$ was similarly determined on whole heart membrane preparations from each of 14 TG4 animals, and plotted against the age of the animal. Ages ranged from 2 to 61 days, and β-AR density ranged from 9.2 to 52.8 pmol/mg.

In the transgenic myocardium, total myocardial β-AR levels rise in a linear manner during the first two months of life (FIG. 2B); this parallels α-MHC expression which at birth is confined to the atria and then progressively increases in the ventricle during the first several weeks of life. The high levels of expression, along with the linear increase during the first two months may also result from further activation of the α-MHC promoter by increased intracellular cyclic AMP (a consequence of β-AR activation); pharmacologic β-AR blockade in vivo has previously been demonstrated to reduce α-MHC expression (P. Pauletto, et al., Am. Heart J. 109, 1269 (1985)).

In situ Detection of $\beta_2$-AR

Figure 3:
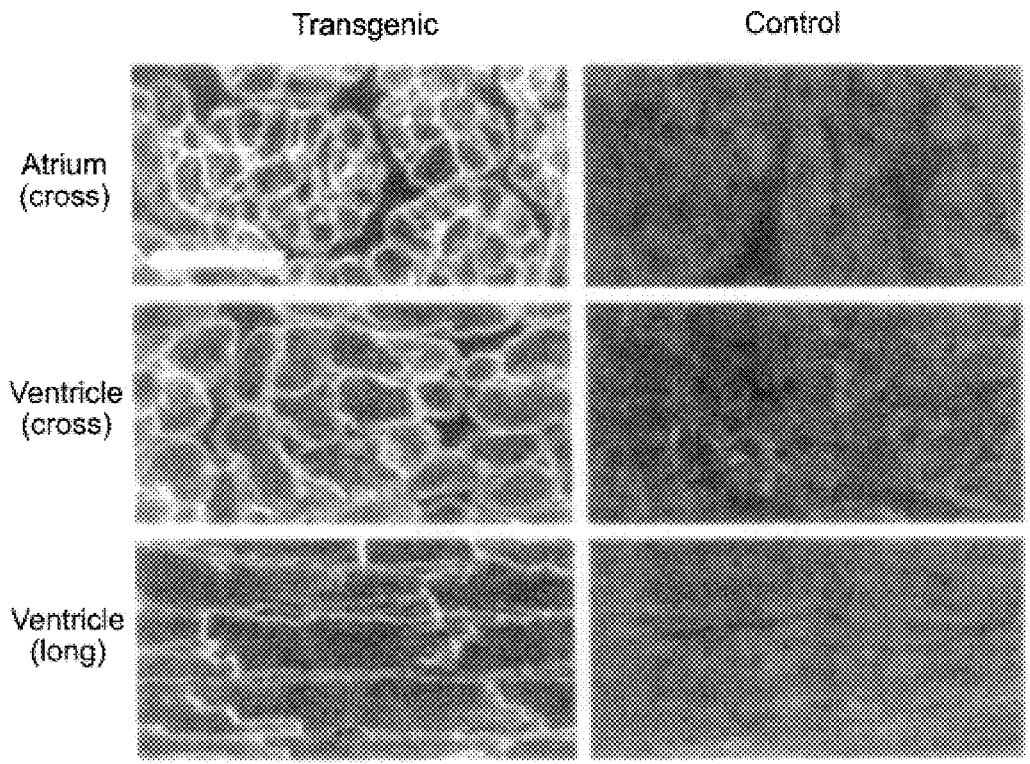
FIG. 3. In Situ Demonstration of Transgene Expression. Immunohistochemical labeling (For direct immunofluorescence micrographs, hearts were rapidly frozen, 7 μm frozen sections cut and fixed in acetone before storage at −20° C. The sections were rinsed 3×3 min. in PBS and 3 min. in PBS with 0.05% Triton X-100(Triton-PBS), then blocked with serum diluent (10% goat serum in PBS with 0.1% bovine serum albumin and 0.1% sodium azide) and rinsed 15 min. in Triton-PBS before overnight incubation at 4° C. in 1:500 of the primary antibody consisting of anti-sera raised to a portion of human $B_2$-AR (M. von Zastrow et al., J. Biol. Chem. 267, 3530 (1992)) in serum diluent. After allowing 2 hrs. to return to room temperature, the sections were washed 4×10 min. in Triton PBS, then incubated 1 hr. in FITC-conjugated goat anti-rabbit IgG diluted 1:50 in serum diluent. Following 3×5 min. rinses in PBS, the sections were mounted in 25 g/L NaI in 1:1 PBS:glycerol and photographed using an Olympus BH-2 microscope.) The sarcolemma of cross-sectioned atrial myocytes was strongly labeled in the transgenic sections and unlabeled in the control. The sarcolemma of cross-sectioned ventricular myocytes was again strongly labeled in the transgenic sections with faint labeling in the control (presumably due to antibody cross reactivity with endogenous mouse β-ARs). Ventricular longitudinal sections revealed strong labeling of the intercalated discs in the transgenic sections but not in the control (size bar=50 µm).

Polyclonal antibodies to the human $\beta_2$-AR (M. von Zastrow et al, 1992) allowed for in situ demonstration of receptor expression in the adult mouse heart (FIG. 3). Consistent with the pattern of αMHC expression, strong labeling was present throughout the atria and ventricles with all myocytes being labeled. Coronary vasculature did not label. Myocyte labeling was confined predominantly to the sarcolemma, including the intercalated discs, with some fainter intracellular labeling which may represent transverse tubules. This in situ demonstration of expression confirmed that the receptor protein undergoes the appropriate post-translational modifications and processing necessary for membrane insertion.

Effect of $\beta_2$-AR Transgene Expression on Adenylyl Cyclase Activity

Figure 4:
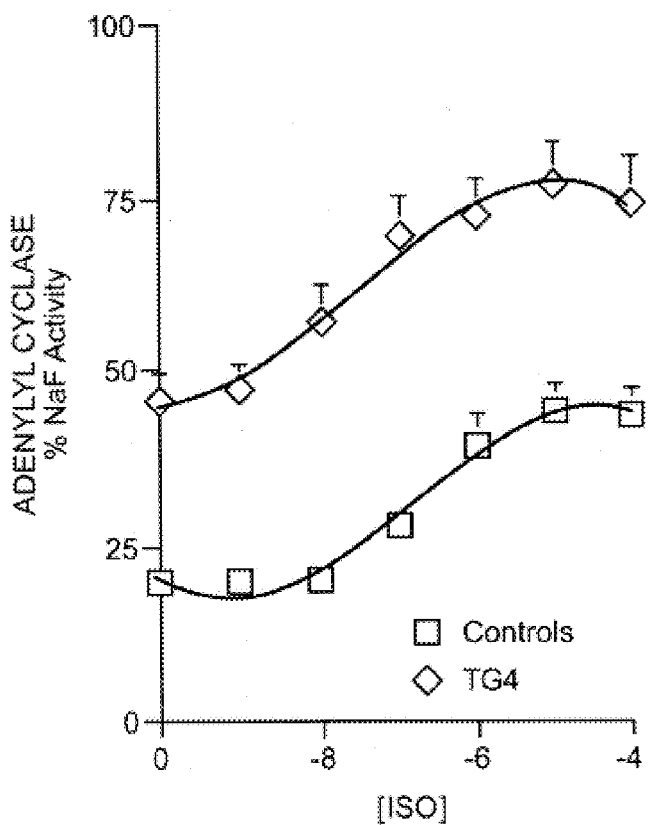
FIG. 4. Adenylyl Cyclase Activity. Membranes were prepared from TG4 hearts and nontransgenic litter mate control hearts as described in FIG. 2. Freshly prepared membranes (5–20 µg protein) were incubated in 50 µl of assay mixture (30 mM Tris Cl, 5 mM $MgCl_2$, 0.8 mM EDTA, 2.7 mM phosphoenolpyruvate, 0.05 mM GTP, 0.1 mM cAMP, 0.12 mM ATP, 1IU myokinase/reaction, 0.2IU pyruvate kinase/reaction, and 3 µCi [α-$^{32}$P]ATP (30 Ci/mmol). Adenylyl cyclase activity was determined under basal conditions, in the presence of progressively higher concentrations of isoproterenol ($1\times10^{-9}$ to $1\times10^{-4}$M) or in the presence of 10 mM NaF. Incubation was for 10 minutes at 37° C., reactions were terminated by the addition of 1 ml of ice cold 0.4 mM ATP, 0.3 mM cAMP, and [$^3$H]cAMP (50,000 cpms/ml). [α-$^{32}$P]ATP was isolated and quantitated as previously described (Y. Salomon et al., Anal. Biochem. 58, 541 (1974)). Basal and isoproterenol stimulated cyclase activities for each membrane preparation were normalized as a per cent of the activity achieved with 10 mM NaF (which maximally activates stimulatory G-protein directly). Mean (±SD) NaF stimulated cyclase activity for the transgenic membranes (445.5±165.5 pmol cAMP/min/mg protein) was not significantly different from that of the controls (606.4±207.8) (Student's t-test p>0.05). Absolute activities parallel the normalized data but with greater variability. Each point on the graph represents the mean±SEM of seven independent experiments each performed in duplicate. The basal and maximal isoproterenol-stimulated values for TG4 were both significantly greater than control values (Students t-test p<0.01). Cricket graph software fitted data to a third order polynomial equation from which $EC_{50}$ values were calculated: the TG4 $EC_{50}$ was $2.2\times10^{-8}$ vs $1.6\times10^{-7}$M for the controls.

The inotropic response resulting from myocardial β-AR stimulation is mediated through activation of adenylyl cyclase and the intracellular second messenger cAMP. To assess whether the myocardium of transgenic animals overexpressing $\beta_2$-AR had enhanced adenylyl cyclase activity, myocardial membranes were incubated with $[^{32}P]ATP$ and the rate of cAMP formation was measured. Basal and isoproterenol-stimulated rates were determined in two transgenic lines (TG4 and TG33) and compared to controls. Both basal and isoproterenol-stimulated cyclase activities were increased in the transgenic animals relative to controls. These increases were most pronounced in TG4 (FIG. 4), which parallels the high level of receptor expression in this line. Increases in basal cyclase activity were the most prominent change and were statistically significant in both TG4 (FIG. 4) and TG33 (data not shown) relative to control values. It should be noted that for TG4 animals, the basal adenylyl cyclase level was as high as the maximal isoproterenol-stimulated level in the controls (FIG. 4). This large increase in basal cyclase is consistent with emerging concepts of receptor action: a small fraction of the total receptor pool is thought to exist in the activated conformation, and is therefore able to couple to G-protein and activate downstream effectors even in the absence of agonist (P. Samama et al., J. Biol. Chem. 268, 4625 (1993)). With the very high levels of receptor present in the transgenics, this small fraction of receptors in the activated conformation under basal conditions becomes quite significant in absolute terms, and effects profound increases in adenylyl cyclase activation. In addition to the absolute increases in basal and isoproterenol stimulated cyclase activity, isoproterenol sensitivity was also enhanced. The isoproterenol dose response curve for TG4 demonstrated an EC50 value which was an order of magnitude lower than the control value (FIG. 4).

Effect of $\beta_2$-AR Overexpression on Myocardial Inotropy

Figure 5A:
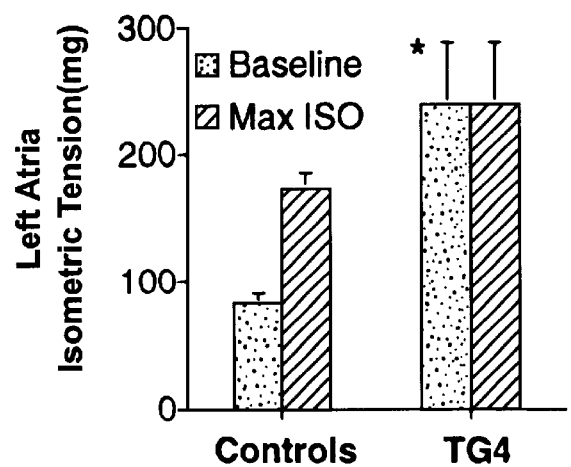
FIGS. 5A–C. Baseline and maximally stimulated responses in isolated atria. Atria were suspended under optimal resting tension in modified Kreb's bicarbonate solution at 30° C. (Mice were anesthetized with pentobarbital 50 mg/kg, the hearts were rapidly excised through a midline thoracic incision; the atria were freed of connective tissue under a dissecting microscope and placed in carbogenated ($CO_2$ saturated) modified Kreb's Bicarbonate solution (MKB). The MKB contained: $NaHCO_3$ 25 mM, NaCl 118 mM, KCl 4.8 mM, $MgSO_4.7H20$ 1.2 mM, $KH_2PO_4$ 1.2 mM, $CaCl_2.2H_2O$ 1.75 mM, Glucose 10 mM, $NaS_2O_5$ 0.1 mM and EDTA 0.03 mM. The MKB also contained: ascorbic acid $1.1\times10^{-4}$M, cocaine $1\times10^{-5}$M, corticosterone $4\times10^{-5}$M and phentolamine $3\times10^{-6}$M, to inhibit autoxidation and neuronal and extra-neuronal uptake and block alpha-adrenergic receptors, respectively. Left atria were paced at 3–7 Hz, with a pulse duration of 3 msec and voltage set at threshold plus 20%, and bathed in a carbogenated mixture. Left atria were paced at the rate exhibited by the spontaneously beating right atria of the same animal. Three responses were studied: left atrial developed tension (FIG. 5A), right atrial developed tension (FIG. 5B) and right atrial heart rate (FIG. 5C). Baseline responses were obtained prior to performing a cumulative concentration response curve to isoproterenol ($1\times10^{-11}$M to $1\times10^{-8}$M). Maximal responses were observed in the presence of $1\times10^{-8}$ isoproterenol. Data are shown as the mean values±SEM for control animals (n=7 or 8) and TG4 animals (n=5 or 6). In all three responses, the baseline values for the TG4 animals were greater than the baseline in the control animals (* P<0.05 Student's t-test), but not different from either control isoproterenol-stimulated values or from TG4 isoproterenol-stimulated values.
Figure 5B:
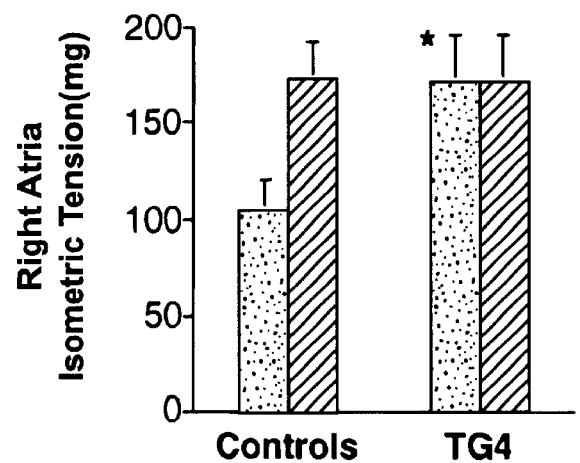
Figure 5C:
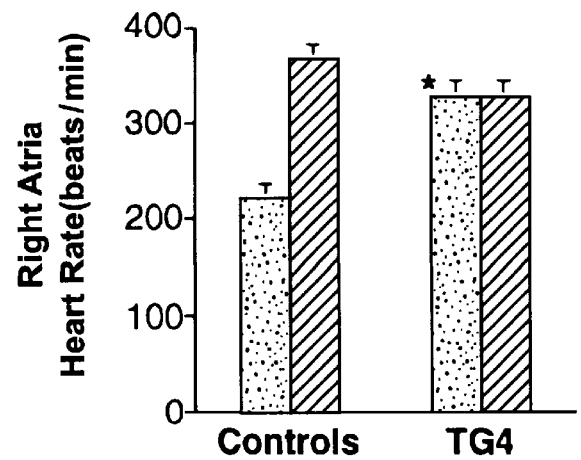

To directly assess the effect of $\beta_2$-AR overexpression on myocardial inotropy, isometric tension development was determined in isolated, perfused atria. Basal isometric tension—development was markedly increased for both the right and left atria of TG4 animals relative to controls (FIG. 5A and B). In the left atria, basal tension was approximately three times that of the control levels. Baseline isometric tension in the transgenics was not different from the maximal isoproterenol-stimulated tension in control atria. Initial studies were conducted at the intrinsic rates of the atria, which were statistically significantly greater in TG4 (FIG. 5C). To eliminate the possibility that this increased rate might be contributing to the increased tension measured in the transgenic myocardium, experiments were conducted to assess the relationship of rate to developed tension. From a rate of 240 to 360 beats/min. (the interval of concern for these studies), a negative force-rate relationship could be reproducibly demonstrated (data not shown) and has previously been described for guinea pig atria (J. R. Blinks et al., *J. Exp. Pharm.* 134, 373 (1961)). These data suggest that measurements of isometric tension at the intrinsic atrial rate may actually underestimate the degree of increased inotropy present in the transgenic atria. In addition, isometric tension was measured in TG33 atria at a rate which did not differ from controls, and a prominent increase in baseline tension was again demonstrated in the transgenic myocardium (data not shown). All atria studied were weighed, and no significant differences were noted between transgenic and control weights.

TG4 atria showed no further inotropic response to doses of isoproterenol which maximally stimulated isometric tension in controls (FIG. 5A and B). This lack of response to isoproterenol in the transgenic myocardium along with the adenylyl cyclase data suggested that even in the absence of agonist, sufficient receptors were present in the activated state to stimulate adenylyl cyclase and effect a maximal inotropic response. Isoproterenol stimulated increases in adenylyl cyclase activity in the transgenic animals; additional increases in inotropy, however, were not generated, presumably because downstream effectors beyond the cyclase became limiting (e.g., calcium channel opening, contractile protein ATPase activity, etc.). While baseline inotropy was equally enhanced in both transgenic lines studied, basal cyclase activation was considerably greater in the higher expressing line (TG4). This suggests that small increases in basal cyclase activity may be sufficient to induce a maximal inotropic response. In addition, there may be β-AR mediated pathways for increasing inotropy independent of cAMP formation. Indeed, myocardial calcium channels, which are coupled directly to stimulatory G-protein, have been identified and probably contribute to the β-AR mediated inotropic response (A. Yatani et al., *Science* 238, 1288 (1987)).

Evaluation of in vivo left Ventricular Functional Changes in β-AR transgenic animals Recent technological advances have enabled cardiac catheterization and hemodynamic measurements in anesthetized mice (H. A. Rockman et al., 1991; K. R. Chien, 1993). To evaluate in vivo left ventricular functional changes, TG4 mice were anesthetized and instrumented. Mice were anesthetized with a mixture of ketamine 100 mg/kg i.p. and xylazine 5 mg/kg i.p. Under a dissecting microscope the animals were placed supine and a midline cervical incision performed exposing the trachea and the carotid arteries. Under direct vision, mice were intubated and connected to a volume cycled rodent ventilator. Either carotid artery was then cannulated with a flame-stretched PE 50 catheter which was connected to a modified P50 Statham transducer. The frequency response characteristics of this catheter-transducer system have been shown to be flat to 30 Hz and adequate for determination of aortic pressure, even with resting heart rates in the mouse of 400–600/min. To minimize vagally mediated reflex changes, bilateral vagotomy was performed in all mice (this did not significantly increase aortic pressure or HR). The chest and pericardium were then opened and a 2F high fidelity micro manometer catheter (Millar Instruments, Houston, Tex.) was inserted into the left atrium, gently advanced across the mitral valve and secured just in front of the valve in the LV. Hemodynamic measurements were recorded at baseline and 45–60 seconds after injection of incremental bolus doses of isoproterenol. Continuous aortic pressures, left ventricular systolic and diastolic pressures and the maximum and minimum first derivative of LV pressure(LV $dP/dt_{max}$ and $dP/dt_{min}$) were recorded on an eight-channel chart recorder and in digitized form on computer disk for beat averaging (codas, Dataq Instruments, Akron, Ohio). Ten sequential beats were averaged for each measurement (CORDAT, Essen, Germany). The dose range of isoproterenol was chosen to have a positive inotropic effect with minimal effect on HR in the control animals. Doses greater than 1 nanogram of isoproterenol resulted in significant lowering of blood pressure and were associated with unreliable measurement of LV $dP/dt_{max}$ (R. R. Taylor et al., 1969). Heart rate (HR), continuous left ventricular (LV) pressures, and aortic pressures were recorded at baseline and after progressive doses of isoproterenol.

Figure 6A:
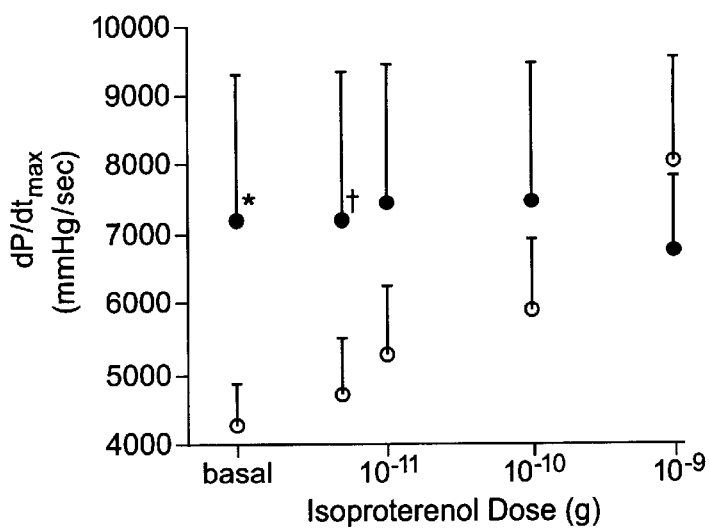
FIGS. 6A–C. In vivo assessment of left ventricular function. Seven TG4 (transgenic) animals and seven controls were anesthetized and instrumented with aortic and left ventricular catheters (Rockman, H. A. et al., Proc. Natl. Acad. Sci. U.S.A. 88, 8277 (1991); K. R. Chien, Science 260, 916 (1993)). Mice were anesthetized with a mixture of ketamine 100 mg/kg i.p. and xylazine 5 mg/kg i.p. Under a dissecting microscope the animals were placed supine and a midline cervical incision performed exposing the trachea and the carotid arteries. Under direct vision, mice were intubated and connected to a volume cycled rodent ventilator. Either carotid artery was then cannulated with a flame-stretched PE 50 catheter which was connected to a modified P50 Statham transducer. The frequency response characteristics of this catheter-transducer system have been shown to be flat to 30 Hz and adequate for determination of aortic pressure, even with resting heart rates in the mouse of 400–600/min. To minimize vagally mediated reflex changes, bilateral vagotomy was performed in all mice (this did not significantly increase aortic pressure or HR). The chest and pericardium were then opened and a 2F high fidelity micro manometer catheter (Millar Instruments, Houston, Tex.) was inserted into the left atrium, gently advanced across the mitral valve and secured just in front of the valve in the LV. Hemodynamic measurements were recorded at baseline and 45–60 seconds after injection of incremental bolus doses of isoproterenol. Continuous aortic pressures, left ventricular systolic and diastolic pressures and the maximum and minimum first derivative of LV pressure(LV $dP/dt_{max}$ and $dP/dt_{min}$) were recorded on an eight-channel chart recorder and in digitized form on computer disk for beat averaging (codas, Dataq Instruments, Akron, Ohio). Ten sequential beats were averaged for each measurement (CORDAT, Essen, Germany). The dose range of isoproterenol was chosen to have a positive inotropic effect with minimal effect on HR in the control animals. Doses greater than 1 nanogram of isoproterenol resulted in significant lowering of blood pressure and were associated with unreliable measurement of LV $dP/dt_{max}$ (R. R. Taylor et al., Journal of Clinical Investigation 48, 775 (1969), H. A. Rockman et al., Proc. Natl. Acad. Sci. U.S.A. 91, 2694 (1994)). Three measured parameters are shown at baseline and after progressively greater doses of isoproterenol (FIG. 6A: LV $dP/dt_{max}$.
Figure 6B:
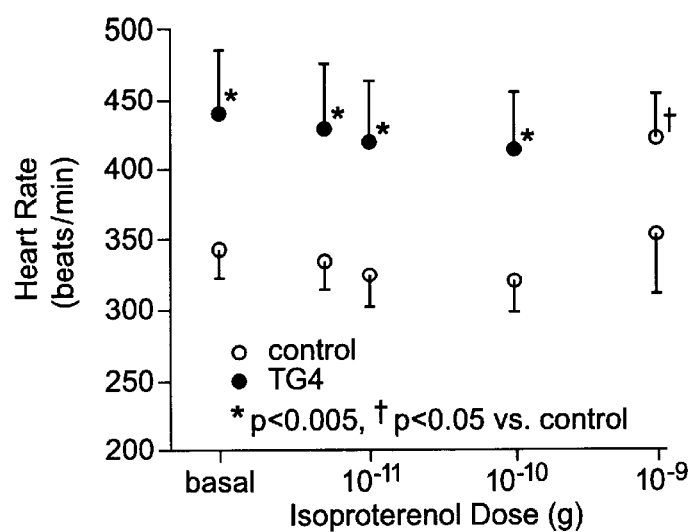
Figure 6C:
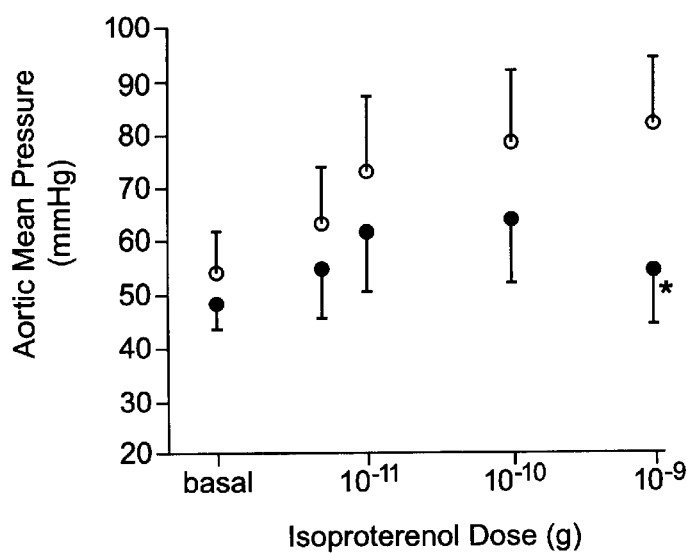

At baseline, while LV end-diastolic pressures (data not shown) and mean aortic pressures (FIG. 6C) were similar between TG4 animals and controls, the maximum first derivative of the LV pressure (LV $dP/dt_{max}$) (FIG. 6A) and HR (FIG. 6B) were significantly increased in the TG4 animals. Baseline maximum LV dP/dt was increased 170% of the control value indicating a markedly enhanced basal inotropic state. In addition, LV relaxation at baseline was also significantly enhanced in the TG4 animals compared to controls as demonstrated by the greater peak negative dP/dt (−5328±1371 vs. −3313±46 mmHg/sec, TG4 and controls, respectively). With the administration of isoproterenol there was no significant change (relative to baseline) in LV $dP/dt_{max}$ or heart rate for the transgenics (FIG. 6A and B), confirming a maximally activated β-AR system. Control animals demonstrated the expected progressive increases in LV $dP/dt_{max}$ following isoproterenol infusion and at the highest doses generated a LV $dP/dt_{max}$ which was not statistically different from TG4 animals (FIG. 6A). Baseline HR was also significantly increased in the TG4 animals and remained greater than the controls throughout the isoproterenol infusion (FIG. 6B). At the highest doses of isoproterenol a statistically significant decrease in the mean aortic pressure was seen in the TG4 animals relative to controls (FIG. 6C), which probably resulted from peripheral β-AR-stimulated vasodilatation uncompensated by further increases in the cardiac output (since the inotropic state of the TG4 LV was already maximal). These data completely support the enhanced basal adenylyl cyclase activity and increased chronotropy and inotropy demonstrated in isolated atria of the TG4 animals.

Figure 7:
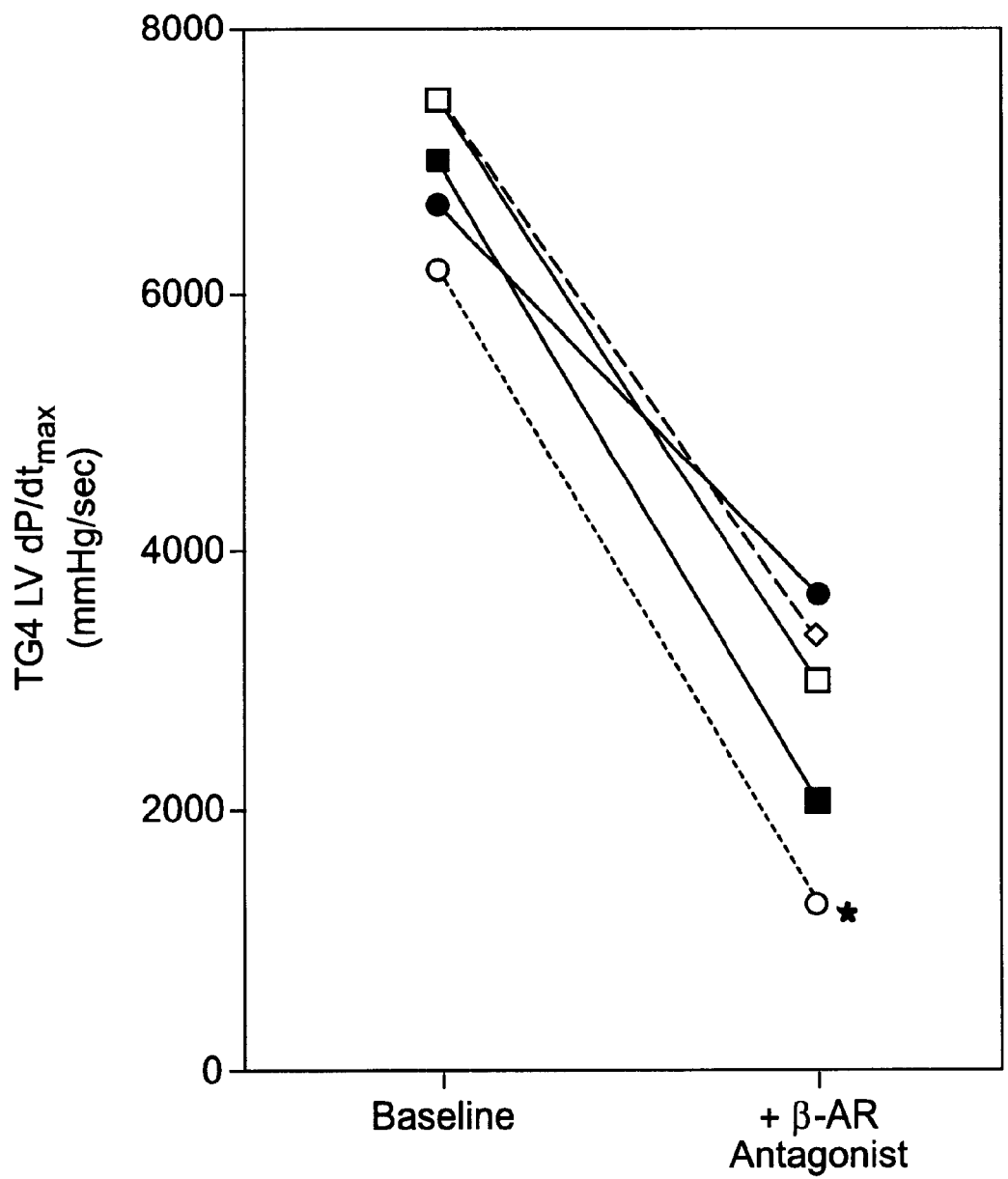
FIG. 7. Effect of administering β-AR antagonist. In separate experiments, LV dP/dt$_{max}$ was determined in TG4 transgenic mice (n=5) at baseline and four minutes after the systemic administration of 5 μg of ICI-118561 (a β-AR antagonist). Asterisks indicate p<0.05, paired Student's T-test.

To demonstrate that the enhanced left ventricular function resulting from the β-AR overexpression, could be regulated in vivo, LV $dP/dt_{max}$ was measured before and after the systemic administration of the $β_2$-AR antagonist, ICI-118551. Marked decreases in the elevated baseline LV $dP/dt_{max}$ were effected in all transgenic animals (FIG. 7B); control animals demonstrated no significant change in response to the administration of this agent (data not-shown). These data demonstrate that the functional enhancement in these transgenic animals can be readily modulated by the systemic administration of a specific β-adrenergic receptor antagonist; the molecular mechanisms by which this antagonist effects these changes probably involves more than the displacement of endogenous catecholamines from the overexpressed receptors (R. A. Bond et al. *Nature* 374, 272 (1995); Samama et al., 1993).

Most importantly, however, these experiments confirm in vivo that the transgenic left ventricle, which serves the critical function of supporting the systemic circulation, has been converted to a maximal inotropic state.

Evaluation of cardiac pathology in β-AR transgenic animals

Given the chronic, marked functional increases which were present in the β-AR transgenic mice, animals were evaluated for the potential development of cardiac pathology. Heart to body weight ratios were minimally altered comparing a large group of transgenic animals to controls. Left ventricular myocyte cross-sectional areas were not significantly increased in the transgenic hearts relative to controls, confirming the absence of hypertrophy. Furthermore, neither fibrosis nor myocyte necrosis were present in transgenic myocardial sections.

Figure 8:
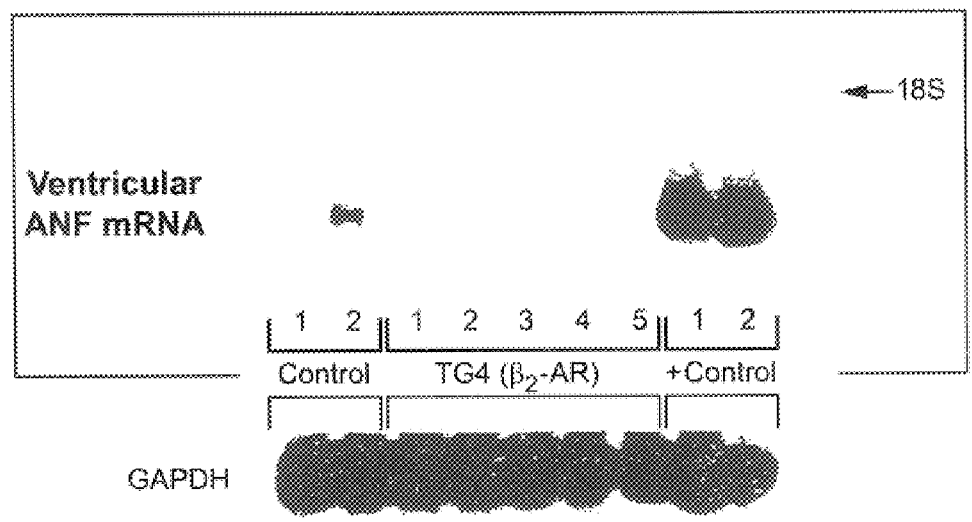
FIG. 8. ANF Northern analysis. Each lane was loaded with 8 μg of ventricular RNA and represents a different animal: control nontransgenic (n=2), TG4 transgenic (n=5), and mice with genetically induced ventricular hypertrophy (positive control, n=2). The blot was probed first with an ANF cDNA probe, and subsequently with a GADPH cDNA probe to demonstrate equivalent RNA loading.

In addition, ventricular ANF mRNA level, a sensitive molecular marker associated with pressure-overload hypertrophy (Chien et al. *Annu. Rev. Physiol.* 55:77–95 (1993)) was assessed by Northern blot analysis (see FIG. 8). Ventricular RNA was extracted, fractionated on a 1% agarose formaldehyde gel, and transferred to a nitrocellulose membrane as previously described (C. A. Milano et al., *Proc. Natl. Acad. Sci. U.S.A.* (1994), in press). Nitrocellulose membranes were prehybridized and then hybridized with a random-primer radiolabeled ANF cDNA probe; blots were stripped and reprobed with the rat glyceraldehyde 3-phosphate dehydrogenase (GAPDH) cDNA probe (Ambion, Austin, Tex.).

A very weak ANF signal was present with normal control ventricular mRNA and mRNA from TG4 animals. Conversely, mRNA from animals with genetically-induced ventricular hypertrophy (C. A. Milano et al., *Proc. Natl. Acad. Sci. U.S.A.*, 1994, in press) characteristically had a very strong signal. Equivalent signals obtained with the GAPDH probe excluded unequal mRNA loading or degradation. Thus, the functional enhancement generated by β-AR overexpression does not effect significant morphologic or histologic alteration. Furthermore, the normal myocyte gene expression appears unaltered.

These results demonstrate the ability to target overexpression of a exogenous, β-AR gene specifically to the myocardium. While some down-regulatory processes may be activated, overexpression of human $β_2$-AR produces dramatic increases in adenylyl cyclase activity, as well as enhanced baseline atrial contractility and left ventricular function.

The instant invention is the first demonstration of genetic engineering as a modality for enhancing myocardial and ventricular function. Given the well-characterized deficiencies in myocardial β-AR numbers and β-AR stimulated inotropy common to virtually all types of chronic heart failure, the clinical relevance of the invention for the study and treatment of heart failure is evident.

The benefits of enhancement of the myocardial β-AR system during heart failure can be further tested given the recent development of a reliable murine model of ventricular failure which can be applied directly to these transgenic mice (H. A. Rockman et al., *Proc. Natl. Acad. Sci. U.S.A.* (1994)). In addition, the utility of transgenic mice in general for studying the functional consequences of altered myocardial gene expression is clear.

These data illustrate that β-AR overexpression results in a significant increase in the absolute amount of receptor in the activated state, which at the tissue or organ level translates into a maintained or constitutive physiologic response, equivalent to the maximal response obtained in agonist-treated control animals. Furthermore, this response can be regulated by the systemic administration of a specific $β_2$-AR antagonist (R. A. Bond et al., 1995). We have previously described the properties of constitutively activated mutated β- and α-ARs (P. Samama et al., *J. Biol. Chem.* 268, 4625 (1993), S. Cotecchia et al., *Proc. Natl. Acad. Sci. U.S.A.* 87, 2896 (1990); Q. Ren, et al., *J. Biol. Chem.* 268, 16483 (1993)), and in other experiments have created transgenic lines expressing these mutated receptors (C. Milano, unpublished material). These receptors are expressed at much lower levels and therefore show less dramatic effects than are observed with overexpression of the wild type receptors in the instant invention. However, it should be emphasized that the biochemical and the physiologic phenotype obtained with the wild type receptors is, in fact, that of a constitutively activated receptor. Thus, the transgenic animals with overexpression of β-AR of the present invention represent a significant advance over what has been previously available. As noted above, even the tiny fraction of overexpressed receptors spontaneously isomerizing to the active state in the transgenic animals is presumably equal to or greater than the total density of active receptors which can be achieved with agonist in the control myocardium.

Given the development of a multitude of tissue specific promoters and the diversity of AR subtypes and functions, the ability to target receptor overexpression to specific tissues represents a novel means of manipulating a broad variety of functions. At the transgenic level this offers a fascinating elemental approach to the study of in vivo physiology. However, as methods for in vivo gene transfer develop (T. Ragot et al., *Nature* 361, 647 (1993); M. A. Rosenfeld et al., *Cell* 68, 143 (1992); R. J. Guzman et al., *Circulation Research* 73, 1202 (1993)), this ability should become applicable to the treatment of disease states where specific receptor-mediated functions are lost or altered.

Recent studies have demonstrated the ability of recombinant, replication deficient adenovirus to transfer genes to the myocardium of adult experimental animals and effect significant levels of expression (Kass-Eisler, A. et al., *Proc. Natl. Acad. Sci. U.S.A.* 90:11498–11502 (1993)). Such an approach may be useful for myocardial β-AR gene transfer, and permit levels of receptor expression capable of enhancing cardiac function. The specific defects in β-ARs and β-AR responsiveness in heart failure make this a particularly attractive potential therapeutic target. Moreover, unlike treatment with receptor agonists, this approach may overcome the limitations of receptor down regulation and desensitization and also avoids the side-effects of agonist activation of receptors in other tissues.

βARK1 transgene and minigene

For the βARK1 transgene; a 5.5 kb SacI—HindIII fragment, the α-MHC promoter, was isolated from clone 20 (A. Subramanian et al., *J. Biol. Chem.* 266, 24613 (1991)) and ligated with the 2.1 kb HindIII—BamHI fragment of bovine βARK1 which had been previously engineered to contain only the coding region (J. Inglese et al., *Nature* 359, 149 (1992)) and inserted as a SacI—BamHI fragment into a plasmid containing the SV-40 intron-poly A signal as described (C. A. Milano et al., *Science* 264, 582 (1994)) to generate pGEM-α-MHC-βARK1-SV-40.

Figure 9A:
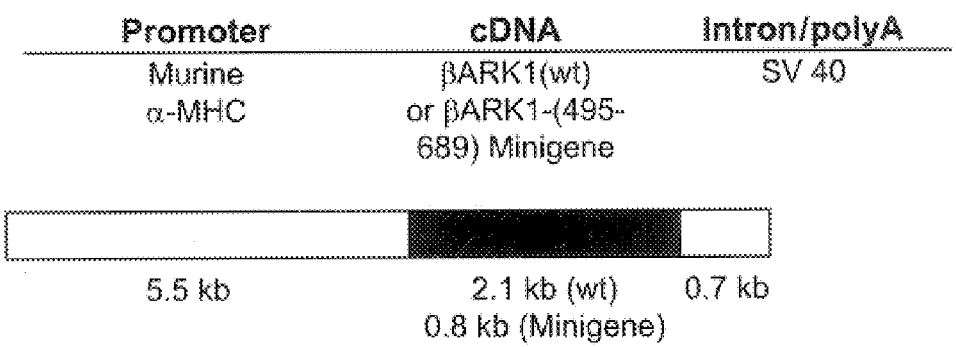
FIG. 9. (A) Transgene DNA constructs for generation of βARK1 and βARK1-(495-689) Minigene mice. (B) Representative Northern blot of RNA extracted from the hearts of control and transgenic mice. 30 μg of total heart RNA was loaded on 1% agarose/formaldehyde gels, electrophoresed, transferred to nitrocellulose and hybridized overnight at 42° C. in hybridization buffer containing 50% formamide and [$^{32}$P]-labeled SV-40 DNA as the probe. The membranes were washed twice in 0.1×saline sodium citrate at 65° C. for 30 min. and subjected to autoradiography overnight at −70° C.

The βARK1-(495-689) Minigene DNA was essentially as described (W. J. Koch et al., *J. Biol. Chem.* 269, 6193 (1994a) and W. J. Koch et al., *Proc. Natl. Acad. Sci., U.S.A.* 91, 12706 (1994b)) except new 5' and 3' restriction enzyme sites were inserted via standard PCR techniques to generate a 0.8 kb SalI—HindIII fragment encoding the last 194 amino acids of bovine βARK1. This fragment was ligated with the 5.5 kb SacI SalI α-MHC promoter fragment into pGEM SV-40 generating pGEM-α-MHC-βARK1-(495-689)-SV-40. The βARK1 and βARK1-(495-689) Minigene transgene constructs (FIG. 9A) were linearized and purified prior to microinjection.

β-ARK1 transgene and minigene constructs

The transgene constructs for the βARK1 and βARK1 inhibitor transgenic animals consisted of the murine alpha myosin heavy chain (α-MHC) promoter ligated to either the entire coding region for bovine βARK1 or the coding sequence for only the last 194 amino acids of βARK1 (βARK1-(495-689) Minigene). This promoter effects specific expression in adult murine atria and ventricles since α-MHC is the predominant cardiac heavy chain isoform expressed. The transgenes were terminated with a portion of the SV-40 intron to improve transcriptional stability (FIG. 9A), as described above.

Figure 9B:
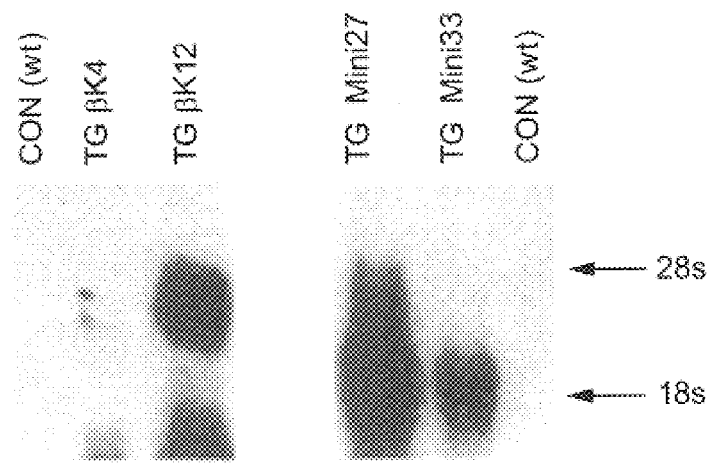

Transgene constructs for βARK1 and the βARK1-(495-689) Minigene were microinjected into the pronuclei of one-cell mouse embryos, which were then surgically reimplanted into pseudopregnant female mice (8, 13, 14). Second generation mice were screened by Northern analysis of heart RNA and two lines for each transgene were established (TGβK4 and TGβK12 for βARK1 and TGMini27 and TGMini33 for the βARK1-(495 689) Minigene) (FIG. 9B). Total RNA was extracted using RNAzol. These animals demonstrated no gross phenotypic changes or unusual neonatal mortality compared to non-transgenic littermate controls. Second generation adult animals 2 to 4 months of age, were used for all biochemical and physiologic studies.

Measurement of βARK activity

Figure 10A:
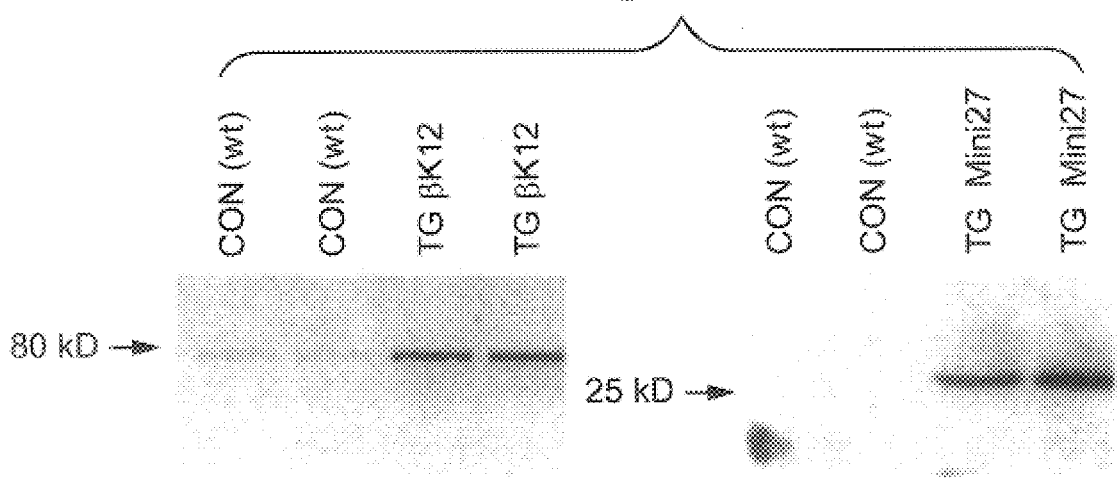
FIG. 10. (A) Western blot analysis of βARK1 and the βARK1-(495-689) Minigene in the hearts of transgenic mice. Myocardial extracts from control or transgenic hearts were prepared and equal amounts of protein (20 to 40 μg) were electrophoresed through 12% SDS/polyacrylamide gels, transferred to nitrocellulose and transgene products were identified with rabbit polyclonal anti-βARK serum raised against a fusion protein of the carboxyl terminus of βARK1 (J. Pitcher et al., Science 257, 1264, 1992; W. J. Koch et al., J. Biol. Chem. 268, 8256, 1993) and chemiluminescent detection of alkaline phosphatase-conjugated secondary antibodies. (B) Assessment of GRK activity in heart extracts from TGβK12 mice. Myocardial extracts were prepared and 50 μg of protein were used in a rhodopsin phosphorylation assay. The top panel is a representative autoradiogram of phosphorylated rhodopsin due to the GRK activity found in two control heart extracts and two TGβK12 extracts. The histogram represents the mean±SEM (n=4) of phosphate incorporation into rhodopsin quantitated on a PhosphorImager (Molecular Dynamics).

The lines with the highest transgene mRNA expression were used to measure myocardial levels of the transgene protein products in both types of animals by Western blotting. Myocardial extracts were prepared essentially as described by M. Ungerer et al., 1993. Whole hearts (100–150 mg) were homogenized in 2 ml of ice-cold lysis buffer [25 mM Tris-HCl (pH7.5), 5 mM EDTA, 5 mM EGTA, 10 μg/ml leupeptin, 20 μg/ml aprotinin and 1 mM phenylmethylsulfonylfluoride]. The crude homogenate was centrifuged for 30 min at 18,000 RPM, pellets discarded and protein concentrations of the supernatants were determined [M. M. Bradford, *Anal. Biochem.* 72, 248 (1976)]. TG,BK heart samples were further purified by taking equal protein amounts in 1.5 ml of supernatant, adding NaCl to a final concentration of 50 mM and 0.75 ml of a slurry of 50% (v/v) diethylaminoethyl Sephacel (pH 7.0). This mixture was incubated on ice for 30 min and poured over an empty small (2 ml) disposable polypropylene column. Final supernatants were eluted with 1 ml of cold lysis buffer and concentrated by filtration in a Centricon 30 (Amicon) microconcentrator.

βARK1 and βARK1-(495-689) Minigene expression was assessed directly from concentrated (Centricon 10, Amicon) supernatants. Marked overexpression of βARK1 was seen in heart extracts from TGβ12 animals (FIG. 10A) while expression of the carboxy terminus of βARK1 was observed in TGMini27 animals (FIG. 10A). The expression was not seen in other tissues.

The activity of myocardial βARK in the transgenic mice was measured by examining the ability of heart extracts to phosphorylate the G protein-coupled receptor rhodopsin.

GRK activity of heart extracts was determined in concentrated supernatants from TGβK and control mice. Total RNA was extracted using RNAzol. Extracts were incubated with rhodopsin enriched rod outer segments (Pitcher et al., 1992; Koch et al, 1993) in 75 μl lysis buffer with 10 mM MgCl$_2$ and 0.1 mM ATP (containing [γ-$^{32}$P]ATP). After incubating in white light for 15 min at room temperature, reactions were stopped with 300 μl ice-cold lysis buffer and centrifuged for 15 min at 12,000 RPM. Supernatants were discarded and the pellets were resuspended in 20 μl lysis buffer and electrophoresed on 12% SDS/polyacrylamide gels. The gels were dried and subjected to autoradiography and phosphorylated rhodopsin was quantitated with a Phosphorlmager (Molecular Dynamics).

Figure 10B:
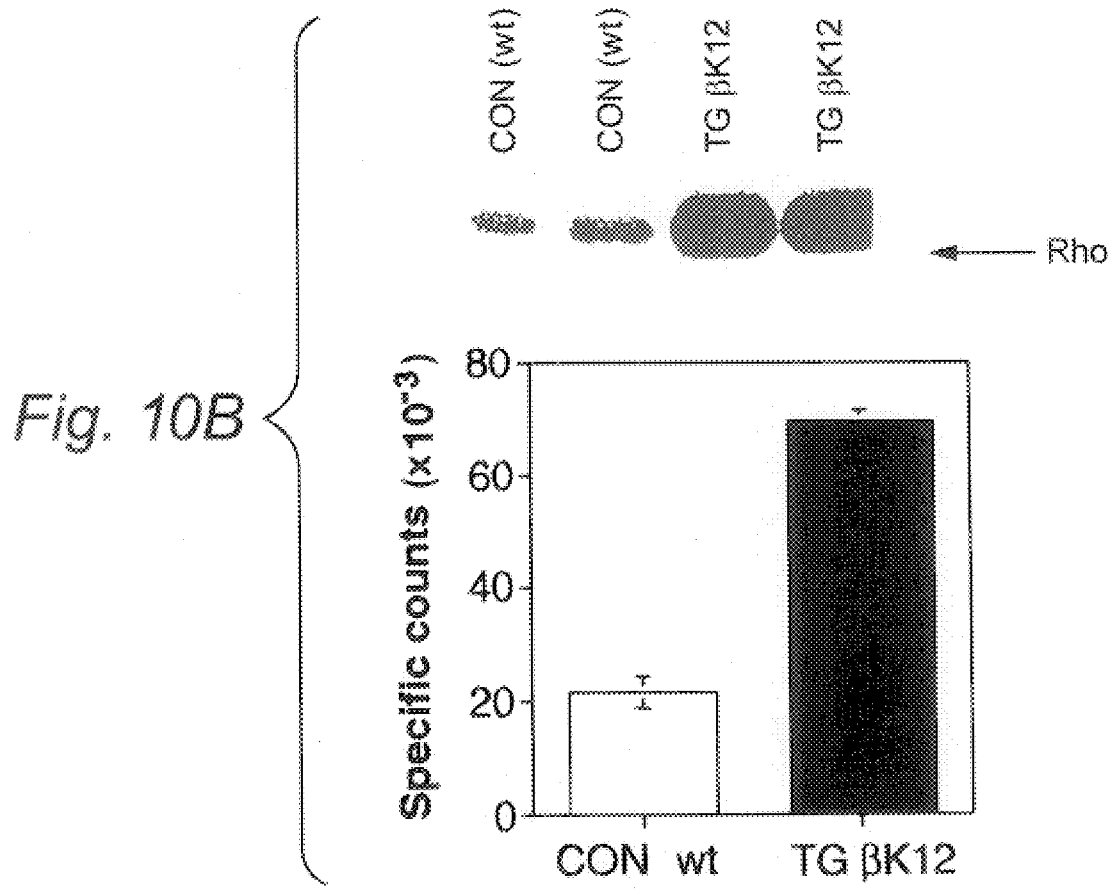

As shown in FIG. 10B, extracts from TGβK12 animals had significantly more kinase activity (>3 fold over controls). TGβK4 mice, which had considerably less mRNA expression (FIG. 9B), catalyzed only a ~50% increase in rhodopsin phosphorylation (data not shown). Thus, overexpression of βARK1 protein translates into enhanced kinase activity. Interestingly, the enhanced βARK1 activity in TGβK12 mice is in the same range as that found in failing heart samples (Ungerer et al., 1993, 1994), which potentially makes these animals a very useful model for testing therapies for the human clinical condition.

Measurement of βARK inhibitory activity

The βARK inhibitory activity of myocardial extracts from TGMini27 mice was examined using similar techniques. Since βARK1-(495-689) Minigene action is expected to reside at the level of $G_{\beta\gamma}$ activation/translocation of βARK (Pitcher et al., 1992, Koch et al., 1993), the above-described rhodopsin phosphorylation assays were carried out with exogenous $G_{\beta\gamma}$ which promotes βARK translocation. Heart extracts (50 μg total protein) from TGMini27 mice expressing the βARK1-(495-689) Minigene displayed similar basal ($G_{\beta\gamma}$ independent) receptor kinase activity to controls (data not shown). However, upon addition of $G_{\beta\gamma}$ (~10 pmoles) to the assay they showed significantly less stimulation of rhodopsin phosphorylation (2.16±0.12 fold over basal, n=5) than controls (3.02±0.31 fold over basal, n=5) (p<0.05, t-test). This indicates that the expressed βARK1-(495-689) Minigene can complete with myocardial βARK for $G_{\beta\gamma}$ binding.

Effect of the βARK gene and βARK minigene on the myocardial β-AR system

In order to examine biochemical effects of the two transgenes on the myocardial β-AR system, receptor-effector coupling in sarcolemmal membranes from hearts of control and transgenic mice was assessed as follows.

Competition binding isotherms in sarcolemmal membranes were carried out using ~80 pM [$^{125}$I]cyanopindolol and varying amounts of isoproterenol in 250 of binding buffer [50 mM HEPES (pH 7.3), 5 mM MgCl2, 0.1 mM ascorbic acid and 75 nM ICI 118,551] with or without 100 μm GTP. Assays were done at 37° C. for 1 hr and then filtered over glass fiber filters, which were washed twice and counted in a gamma counter. Data were analyzed by non-linear least-square curve fitting (P. J. Munson et al., *Anal. Biochem.* 107, 220 (1980)).

Measurements of the total amount of β-ARs indicated that both lines of transgenic mice had similar levels of receptors relative to controls (~45 fmol per mg membrane protein). $\beta_1$ and $\beta_2$-ARs are both present in the mouse myocardium and differ in their ligand binding and effector coupling properties (S. A. Green et al., *Mol. Pharmacol.* 41, 889, 1992). Sarcolemmal membranes were prepared from control mouse hearts and competition binding isotherms were determined for the $\beta_2$-selective antagonist ICI 118,551 against the non-selective radioligand [$^{125}$I] cyanopindolol ([$^{125}$I]CYP). Two binding populations were thus identified: 25% high affinity ($K_i$=0.9 nM; $\beta_2$ subtype) and 75% low affinity ($K_i$=390 nM; $\beta_1$ subtype). Subsequent isoproterenol binding isotherms contained 75 nM ICI 118,551 in order to selectively study $\beta_1$-AR binding, as this concentration inhibits 100% of the $\beta_2$-AR binding component while insignificantly affecting the $\beta_1$-AR component.

Figure 11A:
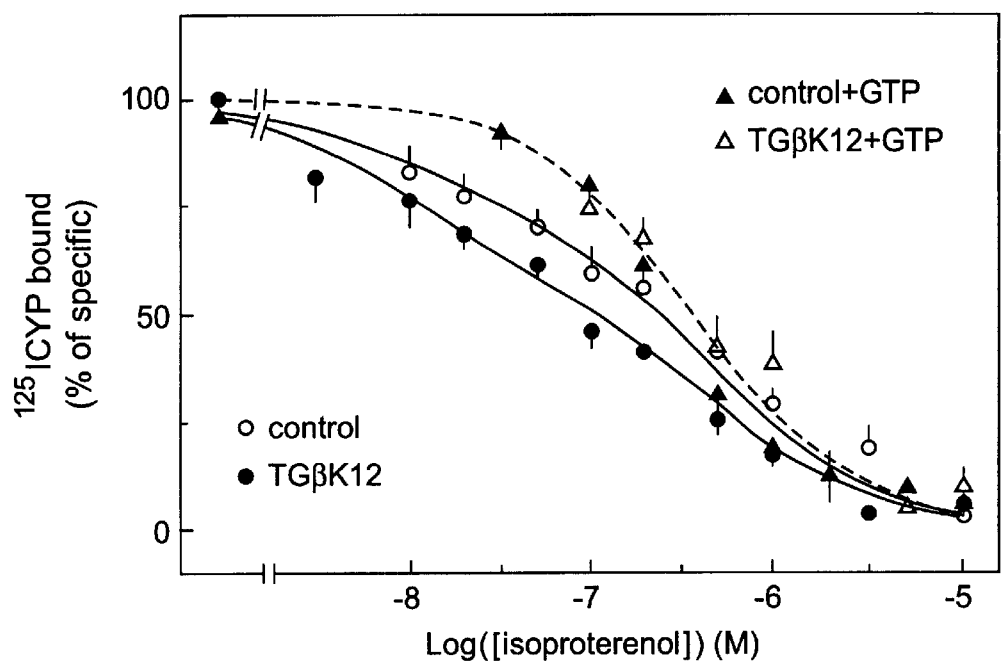

To facilitate the analysis of receptor-effector coupling, we focused on the more abundant $\beta_1$ subtype and examined competition binding isotherms of cardiac $\beta_1$-ARs with the $\beta$-agonist isoproterenol. Control isotherms (FIG. 11A) were biphasic and could be modeled to a high affinity (0.62 nM) and low affinity (32 nM) component. 44% of the receptors were in the high affinity state previously shown to represent a coupled ternary complex of hormone (H), receptors (R) and G protein (G) (1717. R. A. Cerione et al., *Biochemistry* 23, 4519 (1984). (GTP shifted all receptors to the low affinity state. Isotherms from TG$\beta$K12 cardiac membranes were shifted to the right of the control curves (FIG. 11A). GTP caused a further right shift so that the curves were now superimposable on those from control animals in the presence of GTP (FIG. 11A). Computer modeling indicated that these changes were due to a decreased ability of the $\beta_1$-ARs from the TG$\beta$K12 animals to form the coupled H-R-G high affinity state, 28% vs. 44% (p<0.05) with no change in affinity of the receptors. Such changes have previously been demonstrated to occur when receptors are desensitized (R. S. Kent et al., *Mol. Pharmacol.* 17, 14 (1980)).

In contrast, receptor binding isotherms from TGMini27 mice did not differ from controls.

Figure 11B:
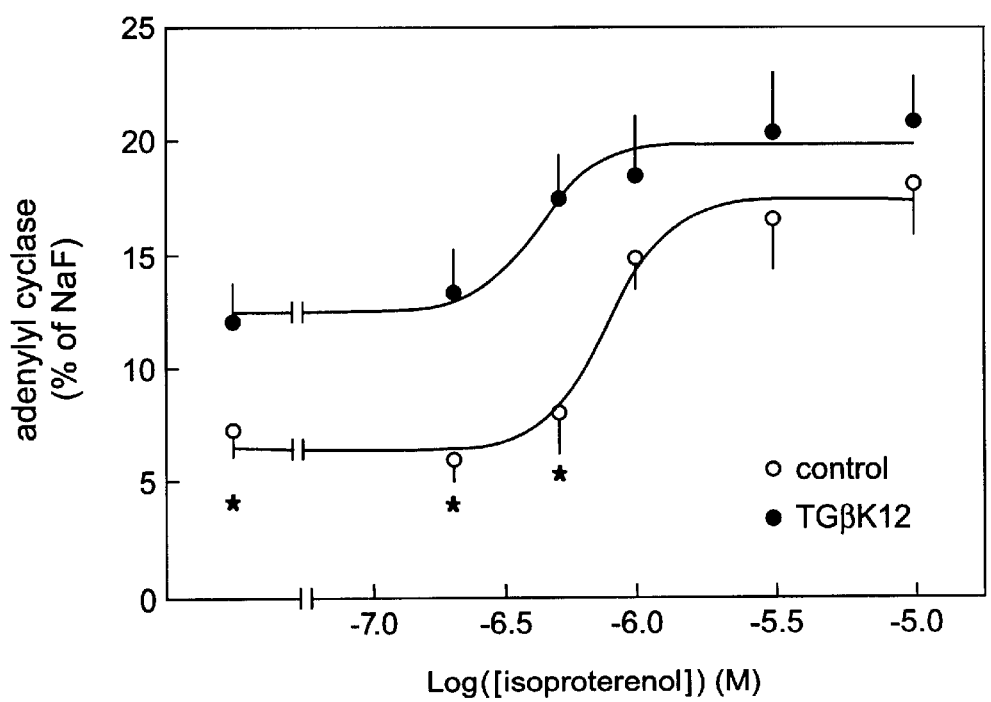

Adenylyl cyclase stimulation is another measure of receptor-effector coupling in sarcolemmal membranes. In cardiac membranes from TGMini27 mice, the cyclase was stimulated by $\beta_1$-ARs to the same extent as in control membranes. In contrast, TG$\beta$K12 mice had significantly lower basal and agonist stimulated cyclase (FIG. 11B). The lower basal cyclase activity seen in TG$\beta$K12 membranes is most likely due to increased phosphorylation of $\beta_1$-ARs by the overexpressed $\beta$ARK in response to normal cardiac sympathetic tone and basal circulating levels of epinephrine.

Thus, functional coupling of the $\beta_1$-AR, as assessed by radio ligand binding and adenylyl cyclase activation, is appreciably hindered by the overexpression of $\beta$ARK1. Perhaps the reason for the absence of any observable difference in $\beta_1$-AR binding or cyclase activation in sarcolemmal membranes from TGMini27 hearts is the fact that in contrast to $\beta$ARK, some of which associates with membranes, the $\beta$ARK1-(495-689) Minigene is an entirely soluble protein which would not be expected to be present in sarcolemmal membranes.

Evaluation of in vivo left ventricular functioning in $\beta$-ARK and $\beta$-ARK minigene animals To directly investigate the effect of $\beta$ARK1 and the $\beta$ARK1-(495-689) Minigene on in vivo myocardial function, cardiac catherization was performed and hemodynamic data recorded on anesthetized mice (Milano et al., *Science* 264, 582 (1994); H. A. Rockman et al., *Proc. Natl. Acad. Sci. U.S.A.* 91, 2694 (1994)).

Left ventricular functional changes were assessed in vivo in TG$\beta$K12 and TGMini27 mice according to the following procedures.

Mice were anesthetized with a mixture of ketamine and xylazine (Milano et al., *Science* 264, 582 (1994)). A cervical incision was made, the trachea intubated and the animal connected to a volume-cycled ventilator. A carotid artery was then cannulated with a flamestretched PE 50 catheter connected to a modified P50 statham transducer. The chest was then opened and a 2F high-fidelity micromanometer catheter was inserted into the left atrium, advanced through the mitral valve and secured in the LV. Hemodynamic measurements were recorded at baseline and 45 to 60 s after injection of bolus doses of isoproterenol. Continuous pressures were recorded on an eight channel chart recorder and in digitized form on computer disk for beat averaging. Ten sequential beats were averaged for each measurement.

Figure 12A:
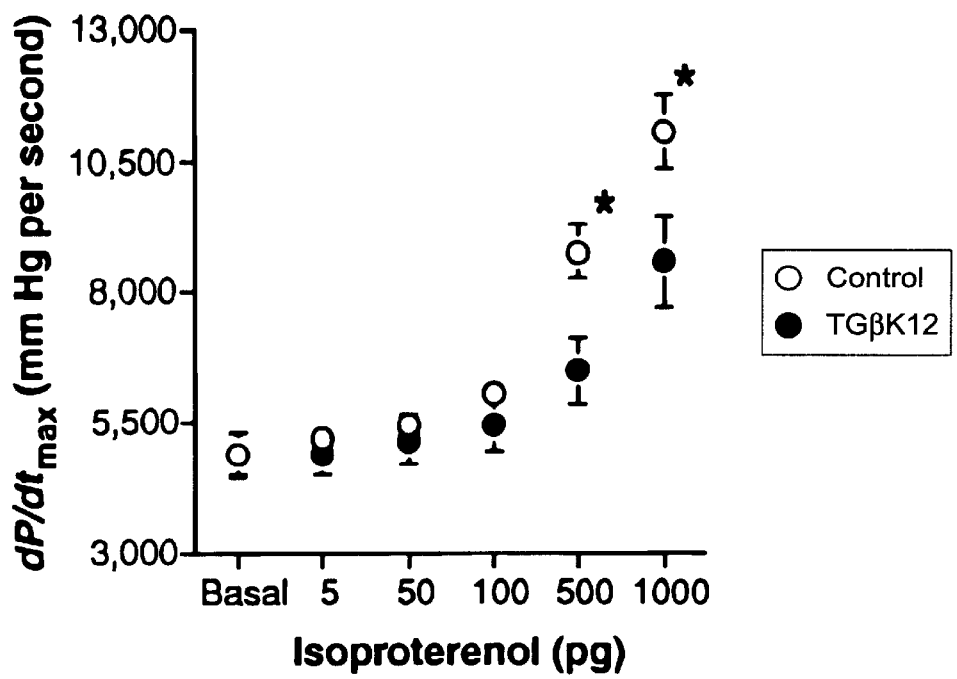
Figure 12B:
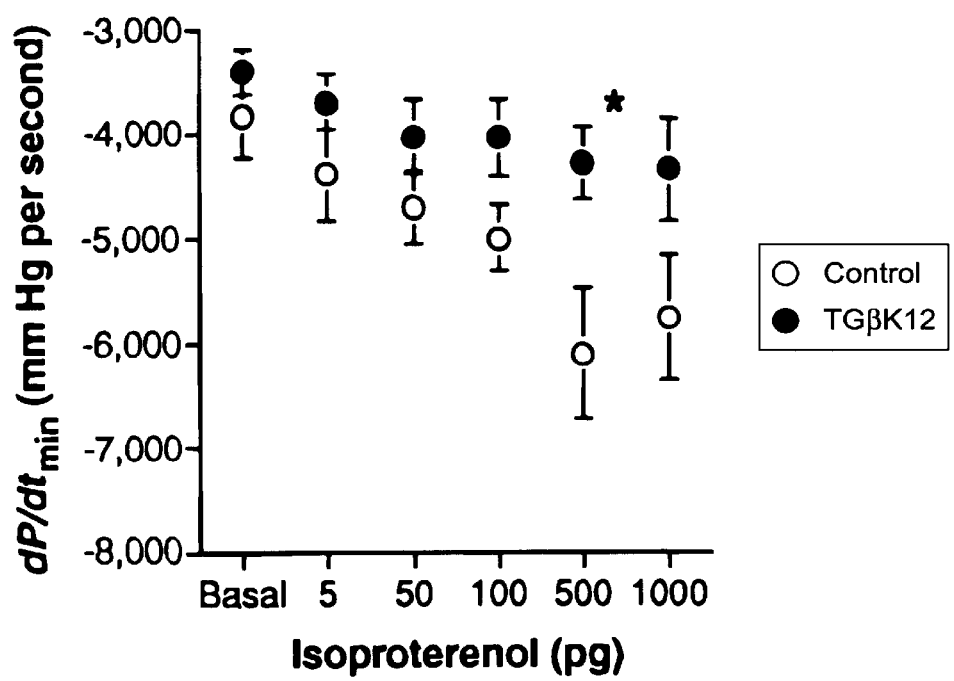
Figure 12C:
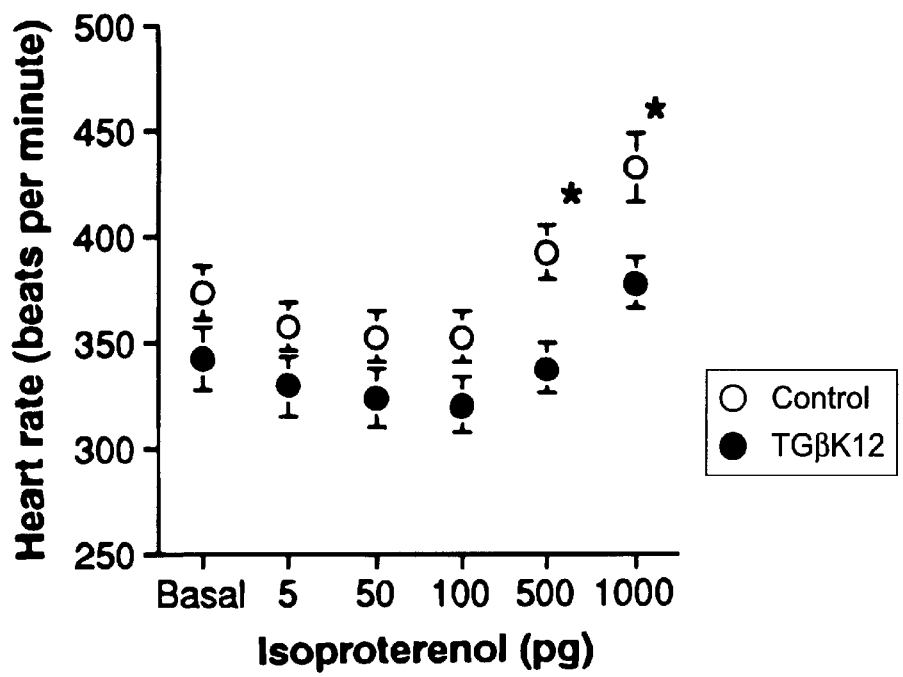
Figure 12D:
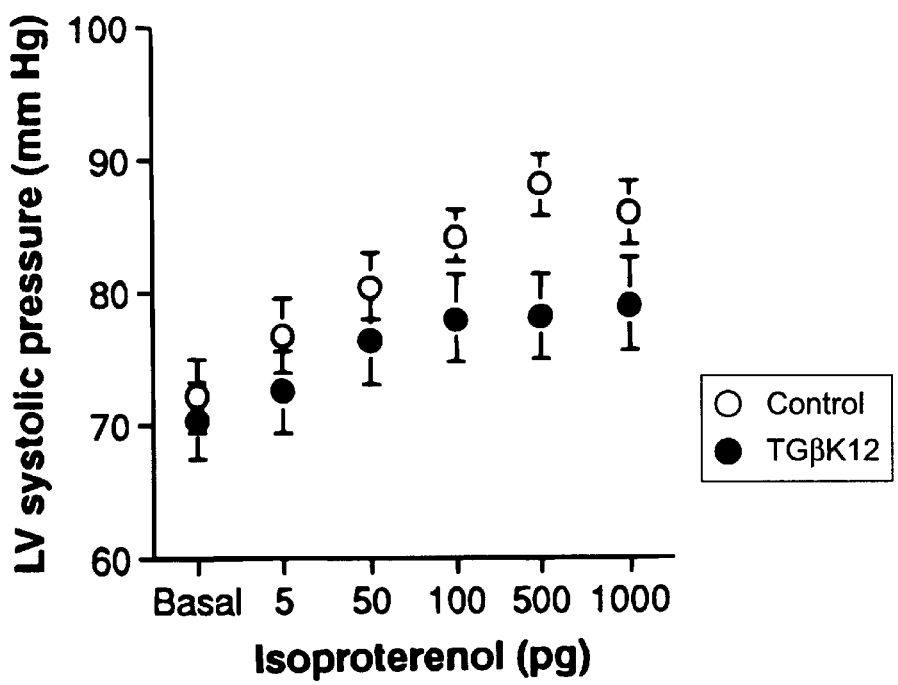

Continuous measurements of heart rate (HR), left ventricular (LV) pressures, and aortic pressure were recorded at baseline and after progressive doses of isoproterenol. For TG$\beta$K12 mice at baseline, HR, the maximum and minimum first derivative of the LV pressure (LVdP/dt$_{max}$ and LV dP/dt$_{min}$) and LV systolic pressure were similar to values in control animis (FIG. 12). However, the inotropic and chronotropic responses to isoproterenol in TG$\beta$K12 animals were significantly reduced (FIGS. 12A–C). Thus, the in vivo effects of overexpressed $\beta$ARK1 mimic those seen in vitro as $\beta$-AR responses to isoproterenol are blunted, presumably due to increased phosphorylation and uncoupling. This is the first demonstration of the physiological consequences of $\beta$ARK1 action in vivo. Moreover, this in vivo data strongly suggests that cardiac $\beta$-ARs ($\beta_1$ and $\beta_2$) are indeed targets for $\beta$ARK1-induced desensitization, an event that is further confirmed by the impaired membrane cyclase responses. The enhanced desensitization of cardiac $\beta$-ARs in TG$\beta$K12 animals suggests that $\beta$ARK1 plays a major role in the regulation of myocardial contractility, supporting the hypothesis that the diminished catecholamine responsiveness seen in heart failure may in fact be due to the observed increase in $\beta$ARK1 expression (M. Ungerer et al., 1993, 1994).

Figure 13A:
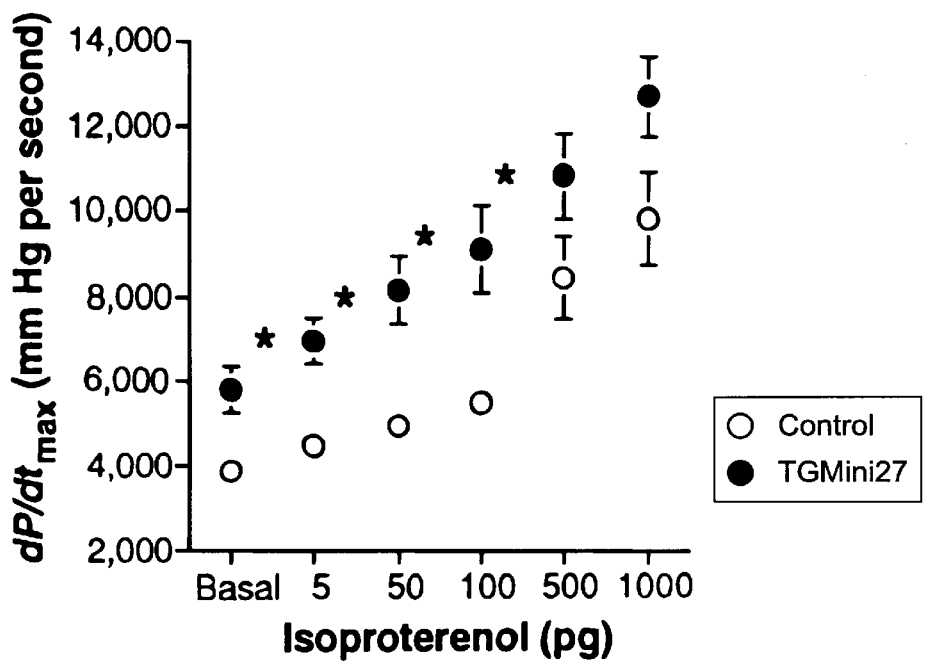
Figure 13B:
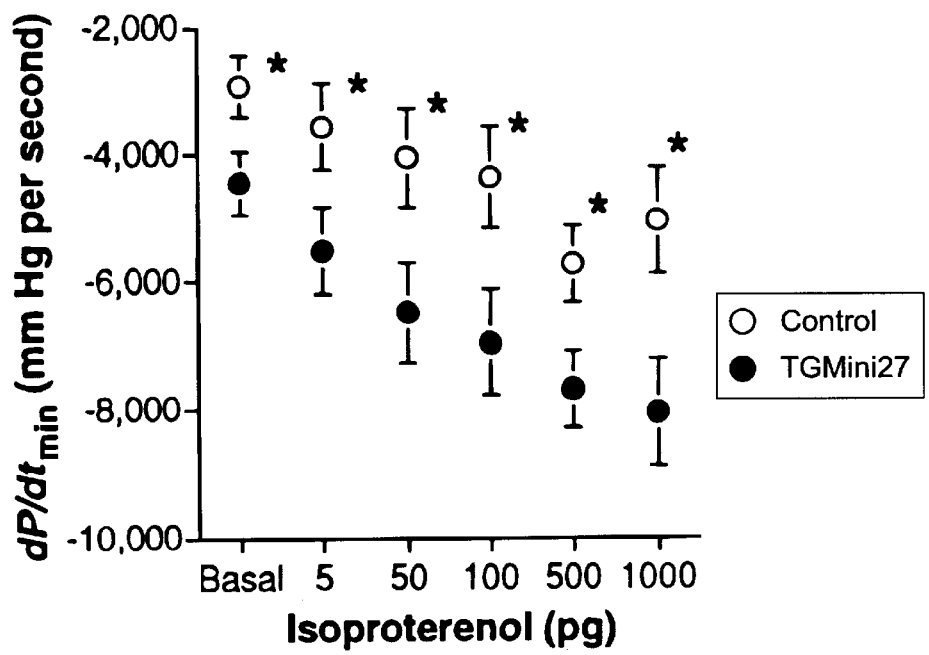
Figure 13C:
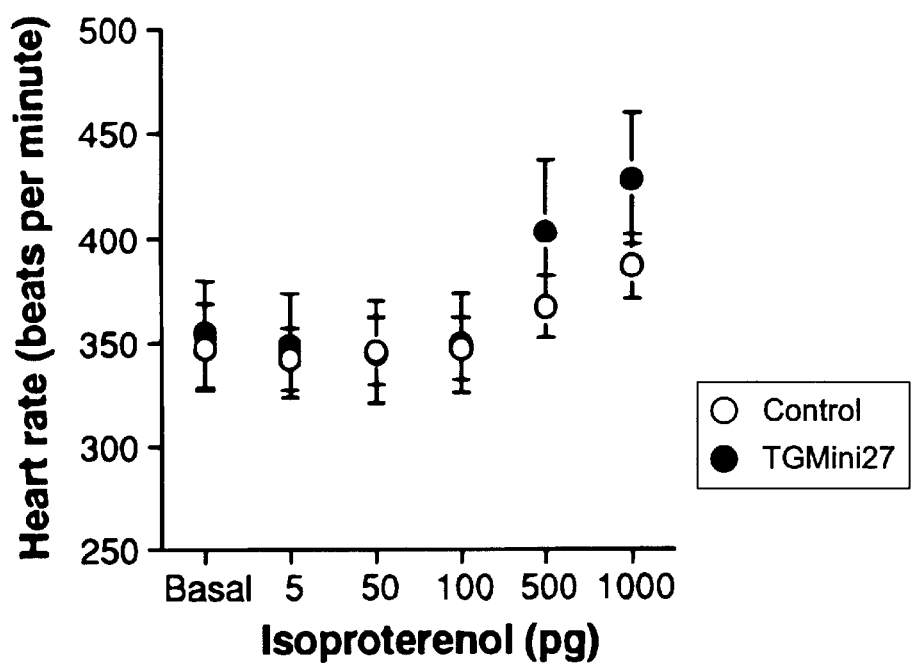
Figure 13D:
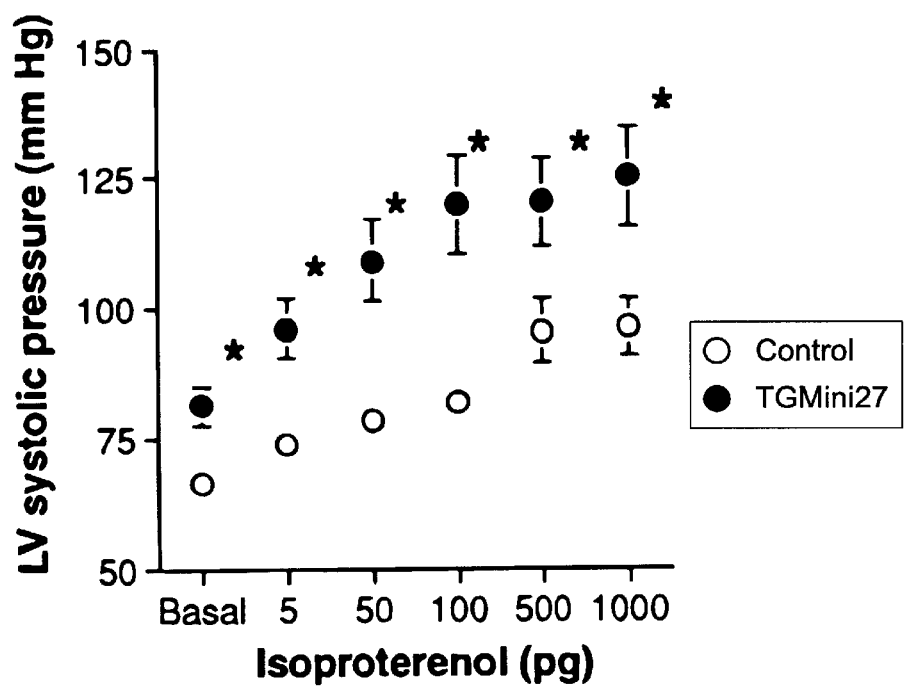

The significance of the role of $\beta$ARK1 in modulating LV contractility was further demonstrated by the remarkable physiological phenotype displayed by the $\beta$ARK1-(495-689) Minigene mice. At baseline, LV dP/dt$_{max}$ (FIG. 13A), LV dP/dt$_{min}$ (FIG. 13B) and LV systolic pressure (FIG. 13D) for TGMini27 mice were all statistically elevated compared to control animals. Left ventricular TGMini27 responses to isoproterenol were also markedly enhanced (FIG. 13A, B and D). Basal HR in TGMini27 mice was similar to controls and only insignificant increases in response to isoproterenol were observed (FIG. 13C).

A second line of mice (TGMini33) expressing the $\beta$ARK1-(495-689) Minigene (FIG. 9B) had essentially the same physiological phenotype (data not shown). Thus, TGMini mice possess a striking cardiac phenotype opposite to that displayed by the TG$\beta$K12 mice indicating that the $\beta$ARK1-(495-689) Minigene is an in vivo $\beta$ARK inhibitor.

The inhibition of $\beta$-AR function by $\beta$ARK1 overexpression and the reciprocal effect of $\beta$ARK inhibition are quite striking when comparing LVdP/dt$_{max}$ values of TGMini27 to those of TG$\beta$K12. For example, after a dose of 500 pg isoproterenol, the mean maximum contractility seen for TGMini27 mice is ~2-fold greater than that for TG$\beta$K12 mice (10,821 mm Hg per sec (FIG. 13A) vs. 6457 mm Hg per sec (FIG. 12A), respectively). LV end diastolic pressure (EDP) was unchanged between either of the two transgenic groups compared to controls suggesting that changes in the LV dP/dt$_{max}$ are not simply due to differences in loading conditions. Maximum LV relaxation in response to isoproterenol was also markedly different between the two transgenic groups as the mean dP/td$_{min}$ at a 1000 pg dose for the TG$\beta$K12 animals was −4350 mm Hg per second (FIG. 12B) while the response in TGMini27 mice was −8071 mm Hg per second (FIG. 13B). Thus, the reciprocal nature of the respective physiologic phenotypes of TGβK12 and TGMini27 mice strongly suggests that the βARK1-(495-689) Minigene is acting through βARK inhibition. These data also suggest the possibility that βARK1 rather than other $G_{\beta\gamma}$-independent GRKs is the principal regulator of the myocardial β-ARs and may indicate a previously unappreciated specifically for βARK.

These results demonstrate that manipulating the activity of βARK1 (both positively and negatively) in the myocardium can greatly influence cardiac function. Overexpression of βARK1 in the heart caused a significant blunting of $\beta_1$-AR mediated adenylyl cyclase response, a decrease in the percentage $\beta_1$-ARs in a high-affinity GTP-sensitive state, and a marked blunting of the inotropic response to isoproterenol. In direct contrast, in vivo myocardial responses to isoproterenol in mice targeted with a βARK inhibition were greatly enhanced. In fact, baseline cardiac function was also markedly enhanced in these animals (TGMini27) demonstrated by the observed 50% increased in basal LV $dP/dt_{max}$. The data taken from both the β-ARK and β-ARK minigene lines of mice strongly suggest that βARK is a critical in vivo modulator of myocardial function (via β-ARs) at baseline and after sympathetic stimulation.

These findings support the concept that increased myocardial βARK1 may be a pathological element in chronic heart failure, since increased βARK1 activity in normal hearts blunted the inotropic response to isoproterenol. This apparently is achieved via a decrease of receptor to G protein coupling, which is reflected in an impairment of high-affinity state formation by $\beta_1$-ARs. These data strongly suggest that the $\beta_1$-AR is a substrate for βARK action which has not been previously documented. Desensitized β-ARs are not limited to chronic heart disease as decreased β-agonist responsiveness has been reported in the myocardium during the process of cardiopulmonary bypass (D. A. Schwinn et al., *Circulation* 84, 2559 (1991); D. Schranz et al., *Circulation* 87, 422 (1993). Thus, the activity of βARK may be a critical regulator of heart function in both chronic and acute settings. The phenotype of TGMini27 mice demonstrates a novel and exciting mechanism for positive inotropy—that is, the inhibition of β-AR desensitization.

Gene Therapy Using β-AR Vectors

Several modes of therapy for patients in heart failure or potential heart failure follow from the finding that increased myocardial function in mammals can be induced by increasing the quantity of β-ARs in myocardial tissue. The objective of such therapy would be to increase the heart function of a patient (e.g. strength of contraction) by at least 10%, and preferably by 20% or more.

A vector comprising a myocardial promoter linked to a β-AR gene can be incorporated into, for example, a viral delivery system and delivered directly to a patient. Delivery can be systemic, for example by oral, intravenous or inhalation routes, or directly, by some form of cardiac perfusion. Several procedures that include gene transfer into cardiac muscle have been described (see, e.g., Kass-Eisler et al, 1993; Stratford-Perricaudet et al., 1993 and Guzman et al., 1993). The gene will then be expressed preferentially or exclusively in cardiac tissue. Viruses suitable for this use include, for example, a replication deficient adenovirus. Dosages can be determined empirically, as is customary in such therapies, by increasing the amount of virus so as to obtain maximal expression while minimizing any toxicity. Virus concentrations in a suitable pharmaceutical preparation might be expected to be from $1 \times 10^9$ pfu/ml to $1 \times 10^{11}$ pfu/ml. Genetic material could also be delivered in liposomes or as naked plasmid DNA.

Another means of therapy is through delivery of transfected myocardial cells to the patient. Cells will be transfected with a vector comprising the β-AR gene and a myocardial promoter and infused into a patient in need of therapy. Cells will then be delivered directly to the heart muscle by techniques similar to other muscle grafts, and would improve cardiac function by supplementation of damaged cells with highly functional ones of the invention.

Gene Therapy Using β-ARK Vectors

The finding that increased myocardial function in mammals can be induced by delivery of a β-ARK inhibitor to myocardial tissue leads to several modes of therapy for patients in heart failure or potential heart failure using these inhibitors. The objective of such therapy would be to increase the heart function of a patient (i.e. improvement in heart rate and/or strength of contraction) by at least 10%, and preferably by 20% or more.

A vector including a myocardial promoter linked to a gene encoding a β-ARK inhibitor can be incorporated into, for example, a recombinant replication deficient adenovirus, and delivered directly to a patient. Delivery can be systemic, for example by oral, intravenous or inhalation routes, or directly, by some form of cardiac perfusion, or by percutaneous catheterization and intra-coronary injection. The gene will then be expressed preferentially or exclusively in cardiac tissue. Viruses suitable for this use include replication deficient adenoviruses and retroviruses. Other methods of delivery for the genetic material, for example via liposomes or naked plasmid DNA, could also be used. Dosages can be determined empirically, as is customary in such therapies, by increasing the amount of virus so as to obtain maximal expression while minimizing any toxicity. Virus concentrations in a suitable pharmaceutical preparation might be expected to be from $1 \times 10^9$ pfu/ml to $1 \times 10^{11}$ pfu/ml. Genetic material could also be delivered in liposomes or as naked plasmid DNA.

Drug Screening

Transgenic mice with increased expression of β-ARK can be used for screening drugs useful for the treatment of heart failure and related conditions. This will be done by measurement of some parameter correlating to cardiac function before and after administration of a test compound. Such testing could be done either in vivo or in vitro (e.g. on the physiology of isolated atria). Indicators that correlate with cardiac function can be physiological or biochemical and include but are not limited to heart rate, strength of contraction, endurance (as measured during some form of exercise). Examples are described in R. A. Bond et al., *Nature* 374, 272 (1995).

β-ARK inhibitor mice can be used to screen for compounds which can reverse the activation of $\beta_1$-ARs ($\beta_1$-selective reverse agonists) in a similar fashion.

The current examples are not meant to be limiting but rather merely illustrative. It will be clear that various modifications can be made and these are intended to be included within the scope of the claimed invention.

What is claimed is:

1. A method of inhibiting the activity of a beta adrenergic receptor kinase 1 (βARK1) so as to improve myocardial function in a mammal, comprising administering to the cardiac muscle of said mammal via cardiac perfusion an effective amount of an expression vector comprising a promoter active in myocardium operably linked to a DNA sequence encoding a βARK1 inhibitor, wherein said inhibitor comprises a βARK1 carboxyl terminal sequence comprising βARK1 residues $Trp^{643}$ to $Ser^{670}$ (SEQ ID NO:1), and wherein expression of said βARK1 inhibitor results in an increase in myocardial function.

2. The method according to claim 1 wherein said promoter is selected from the group consisting of the CMV promoter, Rous sarcoma virus promoter, β-myosin heavy chain promoter, and α-myosin heavy chain promoter.

3. The method according to claim 1 wherein said administration is via intra-coronary injection.

4. The method according to claim 1 wherein said vector is a replication defective viral vector.

5. The method according to claim 4 wherein said viral vector is a replication defective adenoviral vector.

6. The method according to claim 1 wherein said vector is a non-viral vector.

7. The method according to claim 1 wherein said administration is via percutaneous catherization.

8. The method according to any one of claims 1–7 wherein said DNA sequence encodes βARK1 residues 495 to 689 (SEQ ID NO:2).

9. A method of inhibiting the activity of a beta adrenergic receptor kinase 1 (βARK1) so as to improve myocardial function in a mammal, comprising administering directly to the cardiac muscle of said mammal an effective amount of an expression vector comprising a promoter active in myocardium operably linked to a DNA sequence encoding a βARK1 inhibitor, wherein said inhibitor comprises a βARK1 carboxyl terminal sequence comprising βARK1 residues $Trp^{643}$ to $Ser^{670}$ (SEQ ID NO:1), and wherein expression of said βARK1 inhibitor results in an increase in myocardial function.

10. The method according to claim 9 wherein said promoter is selected from the group consisting of the CMV promoter, Rous sarcoma virus promoter, β-myosin heavy chain promoter, and α-myosin heavy chain promoter.

11. The method according to claim 9 wherein said administration is via intra-coronary injection.

12. The method according to claim 9 wherein said vector is a replication defective viral vector.

13. The method according to claim 12 wherein said viral vector is a replication defective adenoviral vector.

14. The method according to claim 9 wherein said vector is a non-viral vector.

15. The method according to claim 9 wherein said administration is via percutaneous catherization.

* * * * *

SEQUENCE LISTING

<160> NUMBER OF SEQ ID NOS: 2

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Protein

<400> SEQUENCE: 1

Trp Lys Lys Glu Leu Arg Asp Ala Tyr Arg Glu Ala Gln Gln Leu Val
 1               5                  10                  15

Gln Arg Val Pro Lys Met Lys Asn Lys Pro Arg Ser
            20                  25

<210> SEQ ID NO 2
<211> LENGTH: 195
<212> TYPE: PRT
<213> ORGANISM: Artificial Sequence
<220> FEATURE:
<223> OTHER INFORMATION: Description of Artificial Sequence: Protein

<400> SEQUENCE: 2

Gly Ile Lys Leu Leu Asp Ser Asp Gln Glu Leu Tyr Arg Asn Phe Pro
 1               5                  10                  15

Leu Thr Ile Ser Glu Arg Trp Gln Gln Glu Val Ala Glu Thr Val Phe
            20                  25                  30

Asp Thr Ile Asn Ala Glu Thr Asp Arg Leu Glu Ala Arg Lys Lys Thr
        35                  40                  45

Lys Asn Lys Gln Leu Gly His Glu Glu Asp Tyr Ala Leu Gly Lys Asp
    50                  55                  60

Cys Ile Met His Gly Tyr Met Ser Lys Met Gly Asn Pro Phe Leu Thr
65                  70                  75                  80

Gln Trp Gln Arg Arg Tyr Phe Tyr Leu Phe Pro Asn Arg Leu Glu Trp
                85                  90                  95

Arg Gly Glu Gly Glu Ala Pro Gln Ser Leu Leu Thr Met Glu Glu Ile
            100                 105                 110

Gln Ser Val Glu Glu Thr Gln Ile Lys Glu Arg Lys Cys Leu Leu Leu
        115                 120                 125

Lys Ile Arg Gly Gly Lys Gln Phe Val Leu Gln Cys Asp Ser Asp Pro
    130                 135                 140

Glu Leu Val Gln Trp Lys Lys Glu Leu Arg Asp Ala Tyr Arg Glu Ala
145                 150                 155                 160

Gln Gln Leu Val Gln Arg Val Pro Lys Met Lys Asn Lys Pro Arg Ser
                165                 170                 175

Pro Val Val Glu Leu Ser Lys Val Pro Leu Ile Gln Arg Gly Ser Ala
            180                 185                 190

Asn Gly Leu
        195